(12) United States Patent
Lal et al.

(10) Patent No.: US 9,173,384 B2
(45) Date of Patent: Nov. 3, 2015

(54) SURGICALLY IMPLANTED MICRO-PLATFORMS AND MICROSYSTEMS IN ARTHROPODS AND METHODS BASED THEREON

(75) Inventors: Amit Lal, Ithaca, NY (US); John Ewer, Valparaiso (CL); Ayesa Kaur, Ithaca, NY (US); Alper Bozkurt, Ithaca, NY (US)

(73) Assignee: Cornell University, Ithaca, NY (US)

( * ) Notice: Subject to any disclaimer, the term of this patent is extended or adjusted under 35 U.S.C. 154(b) by 1295 days.

(21) Appl. No.: 12/518,847

(22) PCT Filed: Dec. 11, 2007

(86) PCT No.: PCT/US2007/025437
§ 371 (c)(1),
(2), (4) Date: Sep. 24, 2009

(87) PCT Pub. No.: WO2008/140502
PCT Pub. Date: Nov. 20, 2008

(65) Prior Publication Data
US 2010/0025527 A1    Feb. 4, 2010

Related U.S. Application Data

(60) Provisional application No. 60/874,433, filed on Dec. 12, 2006.

(51) Int. Cl.
*A61N 1/372* (2006.01)
*A01K 67/033* (2006.01)
*A61N 1/36* (2006.01)

(52) U.S. Cl.
CPC ............ *A01K 67/033* (2013.01); *A61N 1/3605* (2013.01); *A61N 1/372* (2013.01)

(58) Field of Classification Search
CPC ............................ A61N 1/3605; A61N 1/372
USPC .............................................................. 607/2
See application file for complete search history.

(56) References Cited

U.S. PATENT DOCUMENTS

2004/0073273 A1* 4/2004 Gluckman et al. .............. 607/48
2005/0159791 A1* 7/2005 Daly et al. ...................... 607/57

OTHER PUBLICATIONS

Lemmerhirt et al. "A Multitransducer Microsystem for Insect Monitoring and Control." IEEE Transactions in Biomedical Engineering, vol. 55, No. 10, Oct. 2006, pp. 2084-2091.*
HI-MEMS pamphlet, Dr. Amit Lal, published at www.fbo.gov on Mar. 9, 2006, pp. 1-12.*
Ellington, C.P. 1999. The novel aerodynamics of insect flight: applications to micro-air vehicles. The Journal of Experimental Biology. 202:3439-3448.

(Continued)

*Primary Examiner* — Eric D. Bertram
(74) *Attorney, Agent, or Firm* — Perkins Coie LLP

(57) ABSTRACT

A method is provided for producing an arthropod comprising introducing a microsystem such as a MEMS device into an immature arthropod under conditions that result in producing an adult arthropod with a functional microsystem permanently attached to its body. A method is also provided for producing a robotic apparatus. The method can comprise introducing a microsystem such as a MEMS device into an immature arthropod under conditions that result in producing a robotic apparatus with the microsystem permanently attached to the body of the adult arthropod.

19 Claims, 23 Drawing Sheets

(56) References Cited

OTHER PUBLICATIONS

Figure 1:
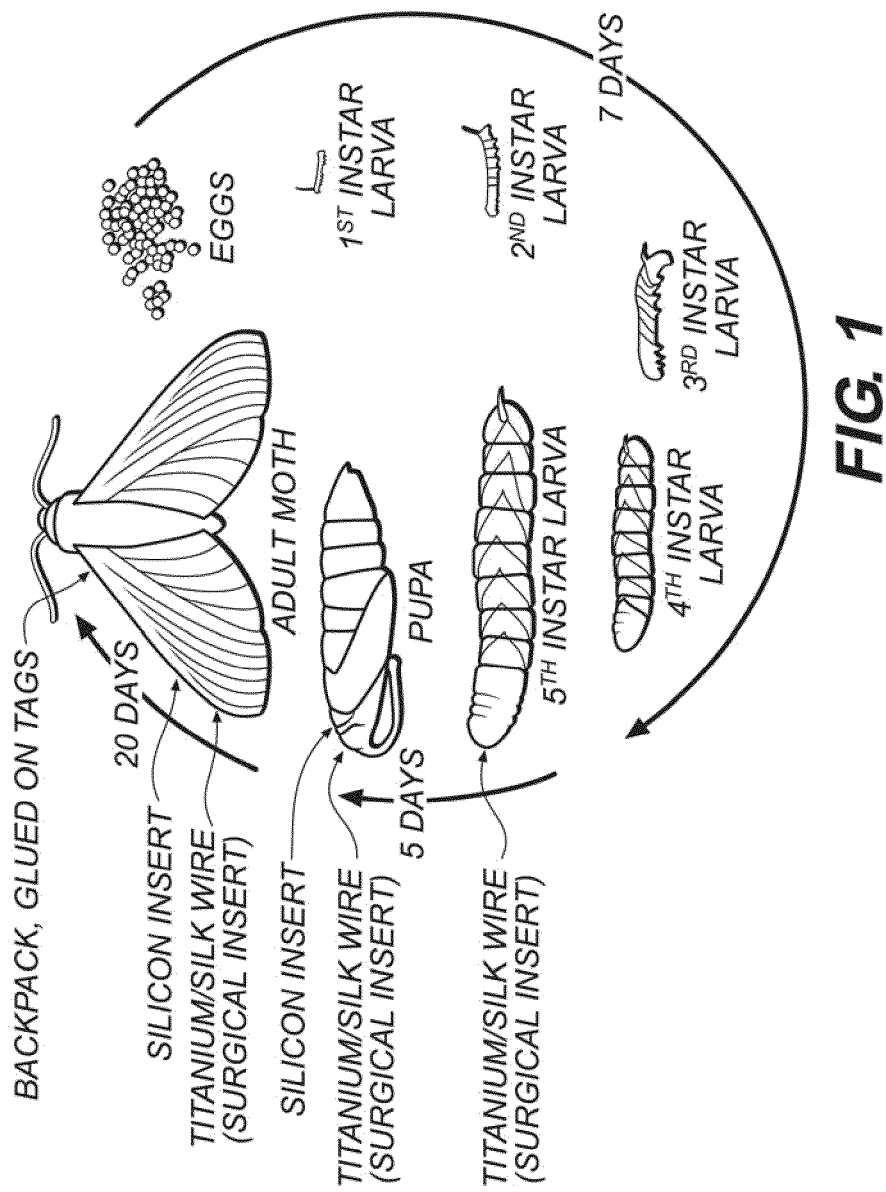
Figure 2D:
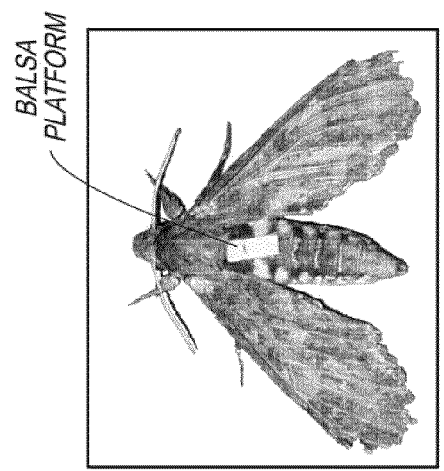
Figure 2C:
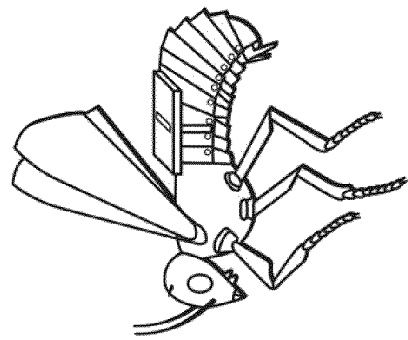
Figure 2B:
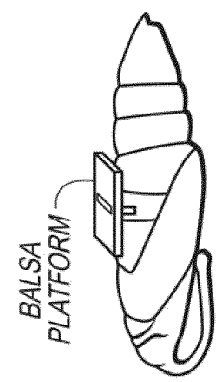
Figure 2A:
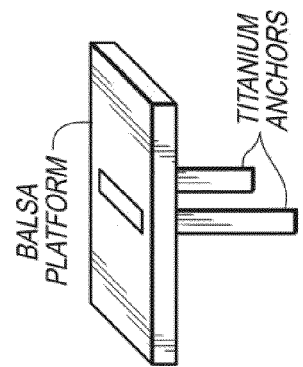

Holzer R. et al. 1997. Locomotion control of a bio-robotic system via electric stimulation. Proc. IEEE/RSJ Internat. Conf. on Intelligent Robots and Systems, Grenoble, France, Sep. 1997, 1514-1519.

Kutsch, W. et al. 1993. Wireless transmission of muscle potentials during free flight of locust. The Journal of Experimental Biology 185: 367-373.

Kuwana, Y. et al. 1999. A radiotelemetry system for muscle potential recordings from freely flying insects. Proceedings of IEEE BEMS/EMBS conf., Atlanta, GA, Oct. 1999: 846.

Mohseni, P. et al. 2001, An ultralight biotelemetry backpack for recording EMG signals in Moths. IEEE Transactions on Biomedical Engineering 48(6): 734-737.

Moore, T.E. et al. 1998. Directed locomotion in cockroaches: Biobots. Acta Entomologica Slovenica 6(2): 71-78.

Paul, Ayesa, et al. 2006. Surgically Implanted Micro-Platforms in Manduca sexta moths, Solid State Sensor and Actuator Workshop, Hilton Head Island, Jun. 2006, pp. 209-211.

Riley, J.R. 2005. The flight paths of honeybees recruited by the waggle dance. Nature 435 (May 12, 2005): 205-207.

Riley, J.R. et al. 1998. Harmonic radar as a means of tracking the pheromone finding and pheromone-following flight of male moths. Journal of Insect Behavior 11(2): 287-296.

International Search Report and Written Opinion of the International Searching Authority for PCT/US2007/25437 mailed Dec. 31, 2008 (9 pgs.).

Loudon, C., 1995. Insect Morphology Above the Molecular Level: Biomechanics. Ann. Entomol. Soc. Am., 88: pp. 1-4.

\* cited by examiner

SILK THREAD INSERTED IN THE THORAX

5TH INSTAR LARVA

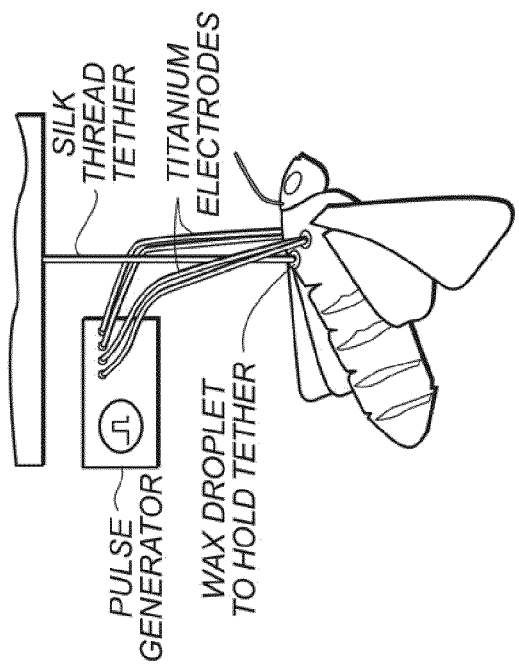
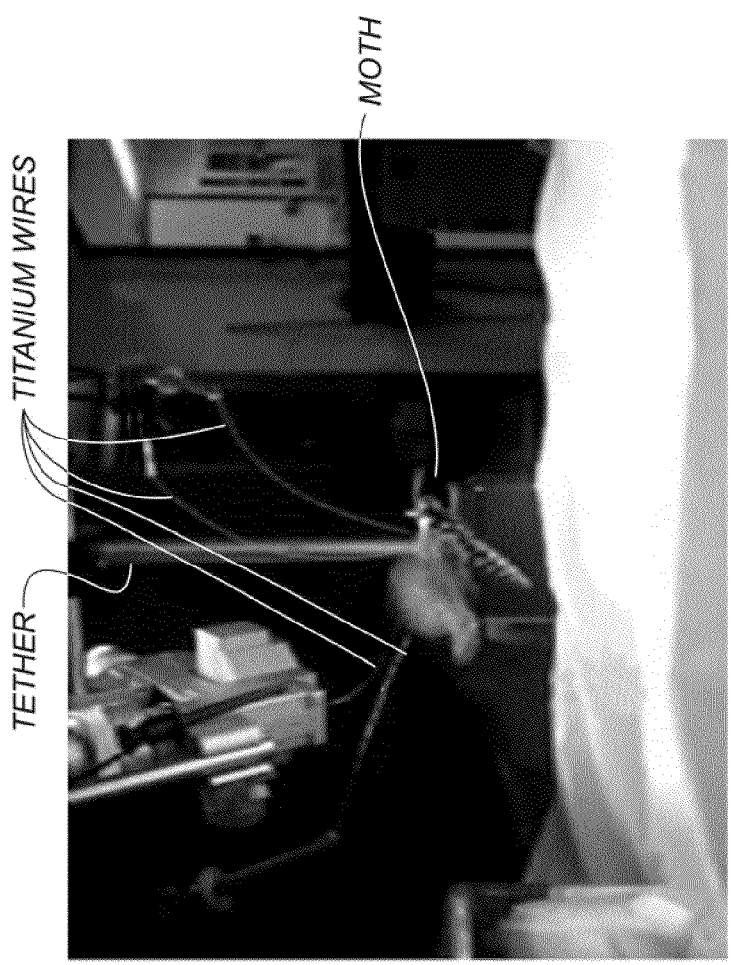
FIG. 17b
FIG. 17a

| STIMULUS DURATION / EXCITED MUSCLE | 5s | 10s | 5s | 40s |
|---|---|---|---|---|
| RIGHT | ON | OFF | OFF | OFF |
| LEFT | OFF | OFF | ON | OFF |

FIG. 21

| COMPONENT | POWER (mW) |
|---|---|
| MICROCONTROLLER | 1.8 |
| LED | 0.6 |
| MUSCLE ACTIVATION | 0.005 |

FIG. 22

US 9,173,384 B2

SURGICALLY IMPLANTED MICRO-PLATFORMS AND MICROSYSTEMS IN ARTHROPODS AND METHODS BASED THEREON

CROSS-REFERENCE TO RELATED APPLICATIONS

This application is a national stage application under 35 U.S.C. §371 of PCT Application No. PCT/US07/025437 filed Dec. 11, 2007, which claims priority to and the benefit of U.S. provisional patent application Ser. No. 60/874,433, filed Dec. 12, 2006, which is incorporated herein by reference in its entirety.

STATEMENT REGARDING FEDERALLY SPONSORED RESEARCH OR DEVELOPMENT

The disclosed invention was made with government support under grant number 0315583 from the National Science Foundation and grant number DAAH01-03-1-R001 from the Defense Advanced Research Projects Agency (DARPA), Microsystems Technology Office. The government has rights in this invention.

REFERENCE TO APPENDIX

Not applicable

1. TECHNICAL FIELD

The present invention relates to methods for producing arthropods bearing functional and permanently attached Microsystems such as MEMS devices. The invention also relates to methods for permanently attaching devices to adult insects. The invention also relates to robotic apparatuses or biobots comprising biological and non-biological system components. The invention further relates to methods for producing robotic apparatuses or biobots comprising biological and non-biological system components. The invention also relates to microprobe microsystem platforms used with robotic apparatuses or biobots.

2. BACKGROUND OF THE INVENTION

Over the past four decades, many attempts have been made to develop small (centimeter-scale) autonomous flying machines (micro-aerial vehicles "MAV" or unmanned aerial vehicles "UAV") for applications ranging from reconnaissance in the battlefield to environmental monitoring. Significant advances in microfabrication technology have made it possible to realize mm-scale low-power microsystems capable of carrying out a wide array of sensing and actuation tasks. These attempts to create mechanical MAVs have ultimately been unsuccessful (Ellington C P, 1999. The novel aerodynamics of insect flight: applications to micro-air vehicles. The Journal of Experimental Biology. 202:3439-348), however, because the power sources needed for powering flight have not been sufficiently miniaturized, even though micro-scale actuators such as MEMS (Micro-Electro-Mechanical Systems), have existed for decades.

Insects can provide models for robotics as "biobots" (Crary, S. B., Moore, T. E., Conklin, T. A., Sukardi, F., and Kotiditschek, D. E. 1996. Insect Biorobotics: Electro-neural control of cockroach walking, Abstr. IEEE Int. Conf. Robotics and Automation, Workshop WT3, Bio-Mechanics, pp. 42-54; Louden, C. 1995. Insect morphology above the molecular level: biomechanics. Ann. entomol. Soc. Am., 88: 1-4), in which an intact (or nearly intact) biological system is incorporated into the design of a microdevice such as a MEMS device (Cary 1996 supra; Louden 1995 supra). Insects are autonomous flying machines and have aerodynamic performance superior to that of existing unmanned mechanical flying machines. Insects also exist in diverse shapes and sizes.

One important challenge that has not been solved, however, has been the permanent attachment of devices to adult insects. Several research groups have glued telemetric and electronic devices onto adult insects to track the insects' movements and migratory paths (Riley J R. 2005. The flight paths of honeybees recruited by waggle dance. Nature 435(12 May 2005): 205-207; Riley J R, Valeur P, Smith A D, Reynolds D R, Poppy G M. 1998. Harmonic radar as a means of tracking the pheromone finding and pheromone—following flight in male moths. Journal of Insect Behavior 11(2): 287-296), and have attached miniature "backpacks" for environmental monitoring, wireless communication, or biobotic manipulation of behavior (Crary 1996 supra; Mohseni P, Nagarajan K. 2001. An ultralight biotelemetry backpack for recording EMG signals in Moths. IEEE Transactions on Biomedical Engineering 48(6): 734-737; Kuwana Y., Ando N., Kanzaki R., and Shimoyama I. 1999. A radio telemetry system for muscle potential recordings from freely flying insects. Proceedings of IEEEBEMS/EMBS conf., Atlanta, Ga., October 1999: 846; Kutsch W, Schwarz G, Fischer H, and Kautz H. 1993. Wireless transmission of muscle potentials during free flight of locust. The Journal of Experimental Biology 185: 367-373).

Attachment of devices to insects as adults, however, leads to reduced flying agility, presumably because the insect perceives the load as a foreign weight (Table 1).

TABLE 1

List of advantages and disadvantages of using robotic MAV and insects as payload carriers.

| | | Advantage | Disadvantage |
|---|---|---|---|
| MAV manual robotics | | 1. Manipulation of flight is possible. 2. Loss of MAV not due to external natural stimuli (pheromone, ultrasound) | 1. Expensive to design and manufacture versatile models. 2. Useful load disappears with decrease in MAV size. |
| Insect as payload carriers | Superficial Attachment | 1. Versatile MAV models. 2. Can carry a load of half its muscle weight | 1. Lack of control of flight direction. 2. Unreliable and prone to dislodge. |

TABLE 1-continued

List of advantages and disadvantages of using
robotic MAV and insects as payload carriers.

| Advantage | | Disadvantage |
|---|---|---|
| Surgical Attachment | 1. Permanent structure for attachment of payload. 2. Versatile MAV models. 3. Can carry a load of half its muscle weight. 4. Acclimatization to the extra load is easier when load is attached at a pre-adult stage. | 3. Light weight power source not available. 1. Lack of control of flight direction. 2. Light weight power source not available |

Telemetric devices glued onto insects are temporary attachments, and have been reported to fall off when the insect is in a confined space or foraging in vegetation. Handling a mobile and active adult insect to attach a payload is also difficult for mass production. Furthermore, with typical adult insect life spans of 2-3 weeks, delivery to the site of deployment at the correct time is challenging.

There is therefore a need in the art for methods for permanently attaching devices to adult insects. There is also a need in the art for unmanned, micro-aerial vehicles with permanently attached telemetric or electronic devices.

Citation or identification of any reference in Section 2, or in any other section of this application, shall not be considered an admission that such reference is available as prior art to the present invention.

3. SUMMARY OF THE INVENTION

A method is provided for producing an arthropod comprising introducing a microsystem into an immature arthropod under conditions that result in production of an adult arthropod, wherein the microsystem is functional and is attached to the body of the adult arthropod. In one embodiment, the microsystem can be permanently attached.

In another embodiment, the immature arthropod can be an insect, crustacean or arachnid.

In another embodiment, the insect can be a holometabolous insect.

In another embodiment, the insect can be a hemimetabolous insect.

In another embodiment, the immature arthropod can be a larva.

In another embodiment, the immature arthropod can be a pupa.

In another embodiment, the immature arthropod can be a nymph.

In another embodiment, the introducing step can be surgical implantation.

In another embodiment, the microsystem can be an attachment apparatus.

In another embodiment, the microsystem can be a micro-platform.

In another embodiment, the microsystem can be a MEMS device.

A method is also provided for producing a robotic apparatus comprising:

a. introducing a microsystem into an immature arthropod (or portion thereof) under conditions that result in production of a robotic apparatus,
wherein the robotic apparatus comprises:
i. the microsystem, and
ii. a biological system, the biological system comprising the adult arthropod (or portion thereof),
and wherein the microsystem is attached to the body of the adult arthropod (or portion thereof).

In one embodiment, the microsystem can be permanently attached to the body of the adult arthropod (or portion thereof).

In another embodiment, the biological system can comprise a portion of the adult arthropod capable of generating or controlling a physiological function of the adult arthropod, and the robotic apparatus is capable of carrying out the physiological function (or a portion or subfunction of the physiological function).

In another embodiment, the physiological function can be selected from the group consisting of locomotion, vision, hearing, chemosensation, temperature sensation, mechanoreception or pressure sensation, acceleration sensation, gravity sensation, magnetic sensation, feeding, digestion, mating and oviposition.

In another embodiment, the microsystem can activate a muscle (or muscle group) that regulates the physiological function.

In another embodiment, the physiological function can be locomotion.

In another embodiment, the muscle (or muscle group) can be flight muscle and the locomotion can be flying.

In another embodiment, the muscle (or muscle group) can be leg muscle and the locomotion can be walking.

In another embodiment, the immature arthropod can be an insect, crustacean or arachnid.

In another embodiment, the insect can be a holometabolous insect.

In another embodiment, the insect can be a hemimetabolous insect.

In another embodiment, the immature arthropod can be a larva.

In another embodiment, the immature arthropod can be a pupa.

In another embodiment, the immature arthropod can be a nymph.

In another embodiment, the introducing step can be surgical implantation.

In another embodiment, the microsystem can be an attachment apparatus.

In another embodiment, the microsystem can be a microplatform.

In another embodiment, the microsystem can be a MEMS device.

An apparatus is also provided comprising:
a. a microsystem; and
b. a biological system, the biological system comprising an adult arthropod (or portion thereof), wherein the microsystem is attached to the body of the adult arthropod (or portion thereof).

In one embodiment, the microsystem can be permanently attached to the body of the adult arthropod (or portion thereof).

In another embodiment, the biological system can comprise a portion of the adult arthropod capable of generating or controlling a physiological function of the adult arthropod, and the robotic apparatus can be capable of carrying out the physiological function (or a portion or subfunction of the physiological function).

In another embodiment, the physiological function can be selected from the group consisting of locomotion, vision, hearing, chemosensation, temperature sensation, mechanoreception or pressure sensation, acceleration sensation, gravity sensation, magnetic sensation, feeding, digestion, mating and oviposition.

In another embodiment, the microsystem can activate a muscle (or muscle group) that regulates the physiological function.

In another embodiment, the physiological function can be locomotion.

In another embodiment, the muscle (or muscle group) can be flight muscle and the locomotion can be flying.

In another embodiment, muscle (or muscle group) can be leg muscle and the locomotion can be walking.

In one embodiment, the immature arthropod can be an insect, crustacean or arachnid.

In another embodiment, the insect can be a holometabolous insect.

In another embodiment, the insect can be a hemimetabolous insect.

In another embodiment, the immature arthropod can be a larva.

In another embodiment, the immature arthropod can be a pupa.

In another embodiment, the immature arthropod can be a nymph.

In another embodiment, the introducing step can be surgical implantation.

In another embodiment, the microsystem can be an attachment apparatus.

In another embodiment, the microsystem can be a microplatform.

In another embodiment, the microsystem can be a MEMS device.

In another embodiment, the physiological function can be flying and the apparatus is a MAV.

A microprobe microsystem platform is also provided. The microprobe microsystem platform can comprise a power layer; a probe layer; and a control layer.

In one embodiment, the power layer can comprise a power source and a switch.

In another embodiment, the power source can be a battery.

In another embodiment, the power layer can comprise a printed circuit board (PCB).

In another embodiment, the control layer can comprise a PCB and a microcontroller functionally connected to the PCB.

In another embodiment, the control layer can comprise an LED.

In another embodiment, the probe can be a microfabricated silicon probe.

In another embodiment, the probe can be positioned between the control layer and the power layer.

In another embodiment, the probe can comprise a plurality of tips, wherein a member of the plurality can be separated from a second member of the plurality by a distance that corresponds to the distance between two cells, tissues or physiological systems of interest.

In another embodiment, the two physiological systems can be two muscles (or muscle groups).

In another embodiment, the two physiological systems can be two neurons (or neural systems, neural centers, or ganglia).

In another embodiment, the probe can be activated by an algorithm whereby sequential electrical pulses are sent to the probe tips.

In another embodiment, the algorithm can comprise outputting time-scheduled square current or voltage pulses.

In another embodiment, the LED on the control layer can be used to monitor electrical excitation generated by the probe.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated or enlarged to facilitate an understanding of the invention.

FIG. 1. Schematic illustration of one embodiment of the method of the invention. Arrows indicate the different stages during the life cycle of a moth (a holometabolous insect) at which a microsystem (a titanium or silk wire, a silicon platform or a microsystem as a backpack) is surgically inserted.

FIGS. 2*a-d*. Schematic diagrams of (a) a titanium-balsa micro-cargo platform, (b) a *Manduca sexta* moth pupa with a platform and wire inserted in the body, (c) an adult *Manduca sexta* moth with a platform, and a photograph of (d) an adult moth with a platform attached with titanium wires. See Example 6.1.

FIGS. 3*a-d*. Schematic diagram of (a) a silicon chip inserted in a *Manduca sexta* pupa and photographs of the ventral abdomen (b) the pupa and (c) the newly emerged adult. (d) The chip bonded intimately with the moth's body tissue when inserted at the pupal stage, and when the chip was removed from the body, tissue was torn away along with the chip. See Example 6.1.

FIGS. 4*a-d*. Photographs of (a) a titanium and balsa wood micro-cargo platform, (b) late stage *Manduca sexta* pupa bearing a titanium and balsa wood micro-cargo platform attached to the abdomen, (c) newly emerged adult with the titanium and balsa wood micro-cargo platform, and (d) scanning electron micrograph (SEM) showing tissue growth on the titanium wire inside the abdomen of the adult (wire was inserted at the late pupal stage). Such tissue growth produces a strong and reliable attachment of the microsystem due to tissue support. See Example 6.1.

FIGS. 5*a-d*. Photographs of a silicon chip (2×4 mm) inserted into (a) the ventral abdominal segment of a late pupa, (b) schematic of a silicon insert in a late pupa, (c) the adult after emergence with the silicon insert, and (d) a SEM photograph of a silicon chip in a two-day old adult (silicon chip inserted at the late pupal stage). See Example 6.1.

FIGS. 6a-d. Schematic diagram of (a) silk thread insert transplanted into a fifth instar *Manduca sexta* larva. Photographs of (b) silk thread inserted in a larva, (c) silk thread inserted in a pupa and (d) silk thread in an adult after emergence. Such silk thread inserts can be used as tethers to attach a micro-cargo to the adult moth. See Example 6.1.

Figure 7C:
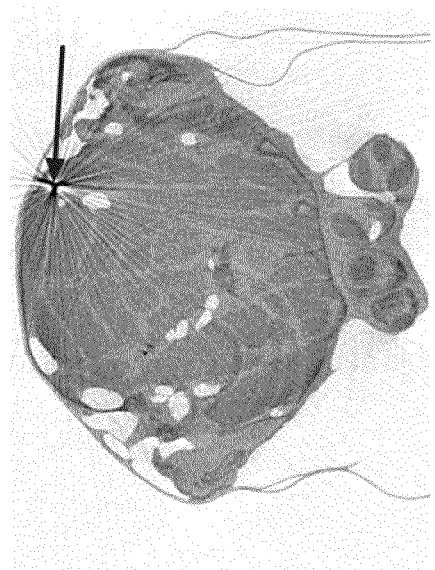
Figure 7B:
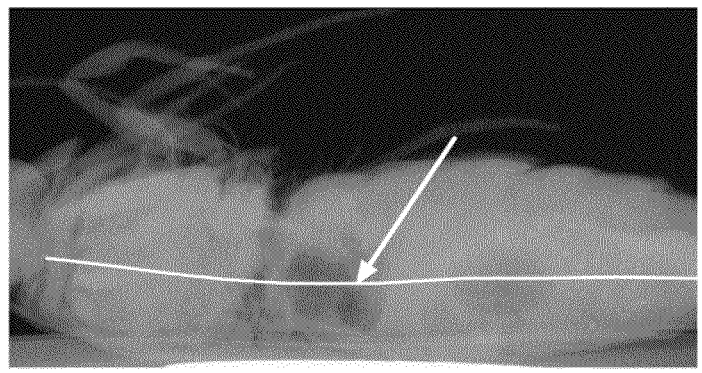
Figure 7A:
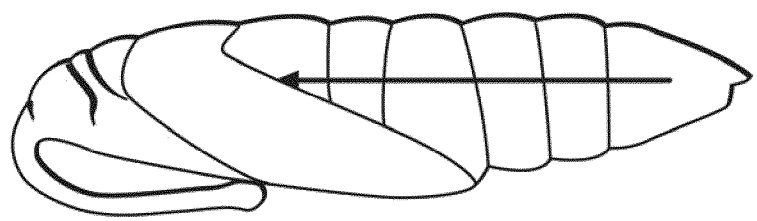

FIGS. 7a-c. Schematic diagram of (a) insertion of a titanium wire through the posterior end distal end of the abdomen of a *Manduca sexta* pupa and running anterior-posterior in the abdomen. (b) X-ray scanned image of the emerged adult moth with the wire, (c) MCT-scanned image of a cross-section of the adult through the thorax showing the wire embedded within the flight muscle tissue. See Example 6.1.

Figure 8:
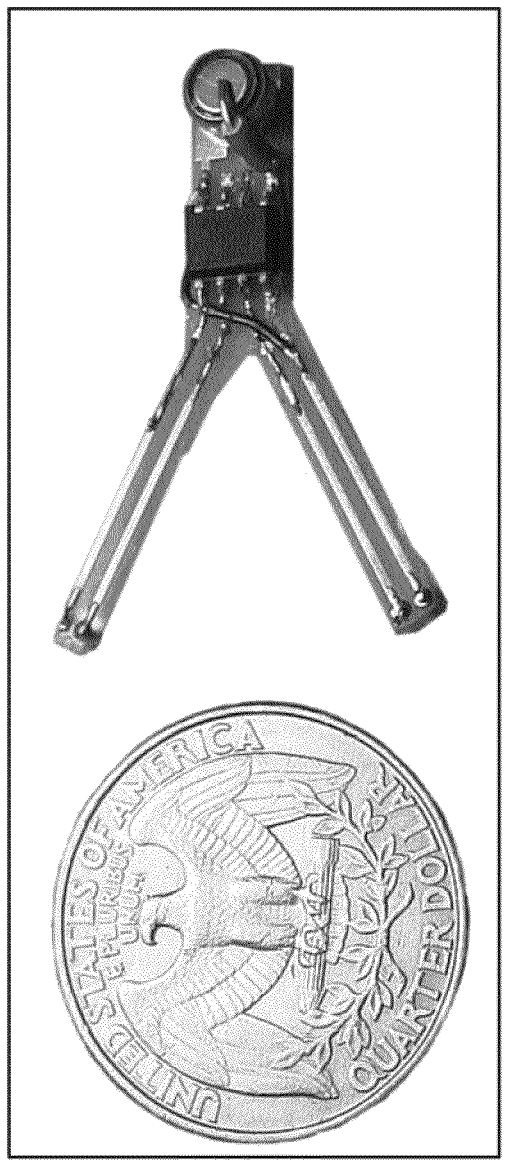

FIG. 8. Circuit board with a miniature LED-based device to regulate direction of flight in an adult moth. See Example 6.1.

Figure 9:
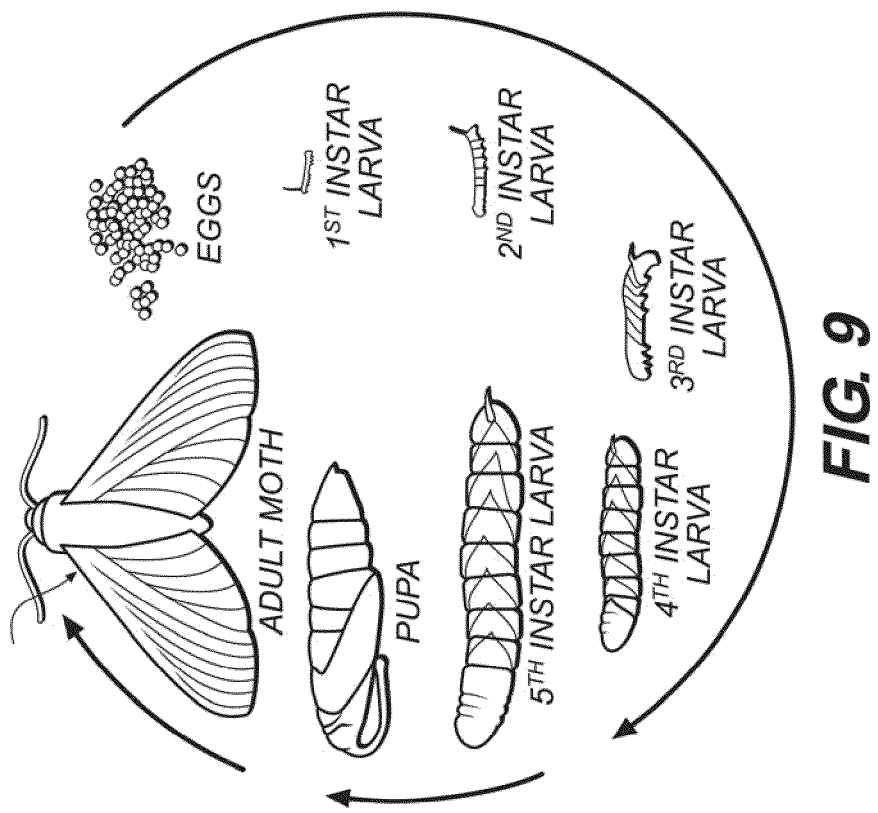

FIG. 9. Schematic diagram of the *Manduca sexta* lifecycle, indicating the site and stage for insertion of a biocompatible microfabricated microcontroller-based electrical probe for flight muscle actuation (shown with arrows). See Example 6.2.

Figure 10:
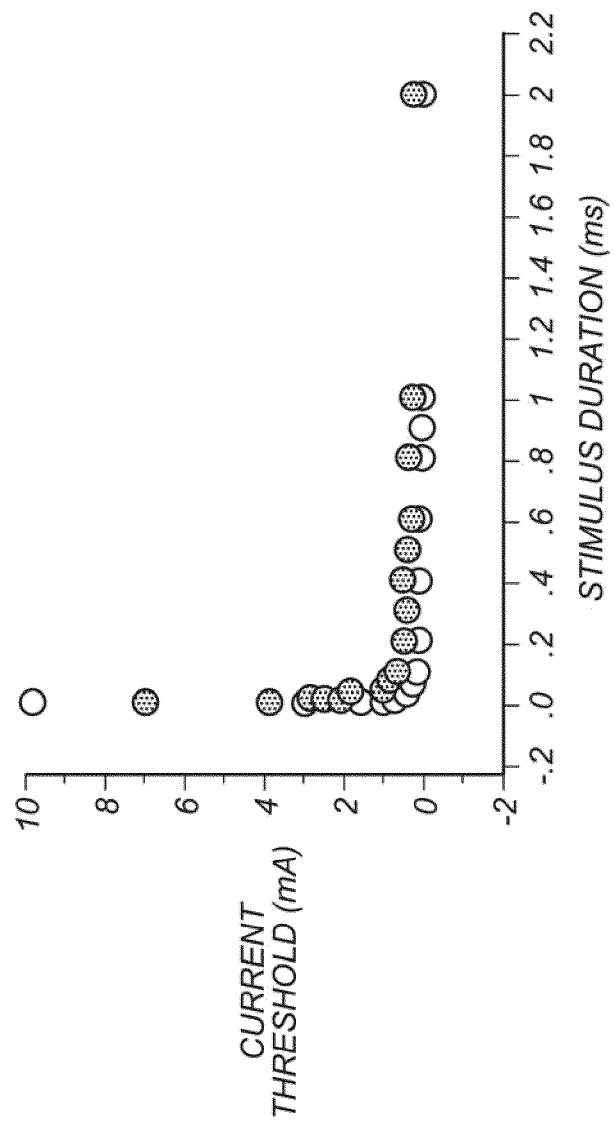

FIG. 10. Plot of current threshold (mA) for muscle activation (mA) versus various stimulus durations (ms). See Example 6.2.

Figure 11A:
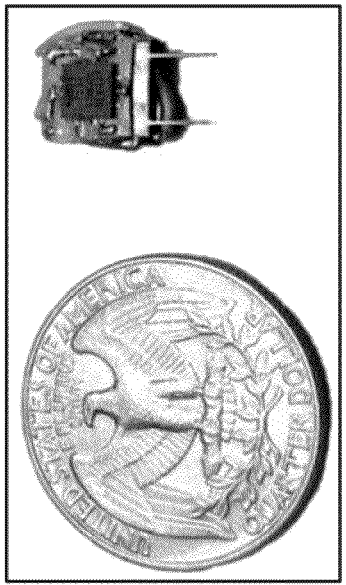
Figure 11B:
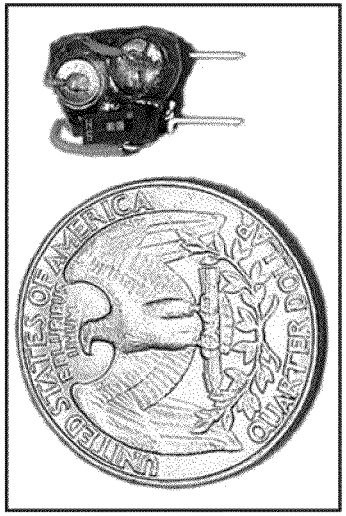
Figure 11C:
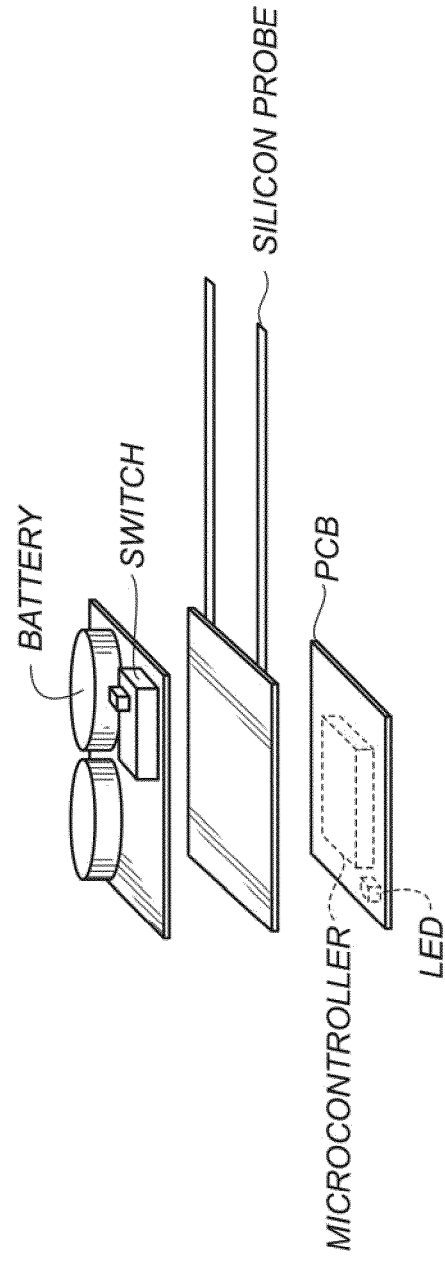

FIGS. 11a-c. Microfabricated platform. (A) front views. (B) back view. (C) schematic of different layers of the platform. See Example 6.2.

Figure 12:
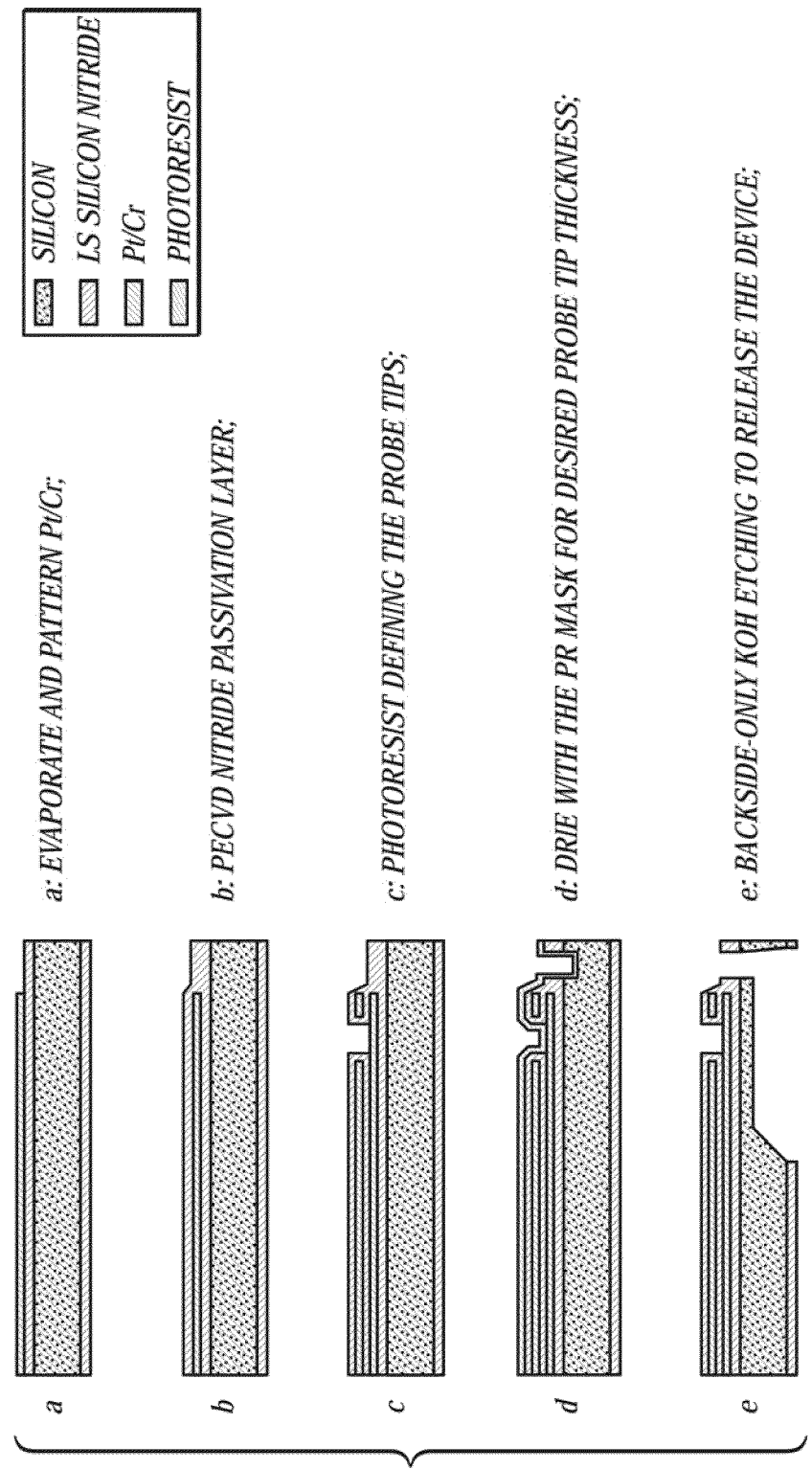

FIG. 12. Schematic diagram of the fabrication process of a microfabricated microcontroller-based electrical probe. See Example 6.2.

Figure 13:
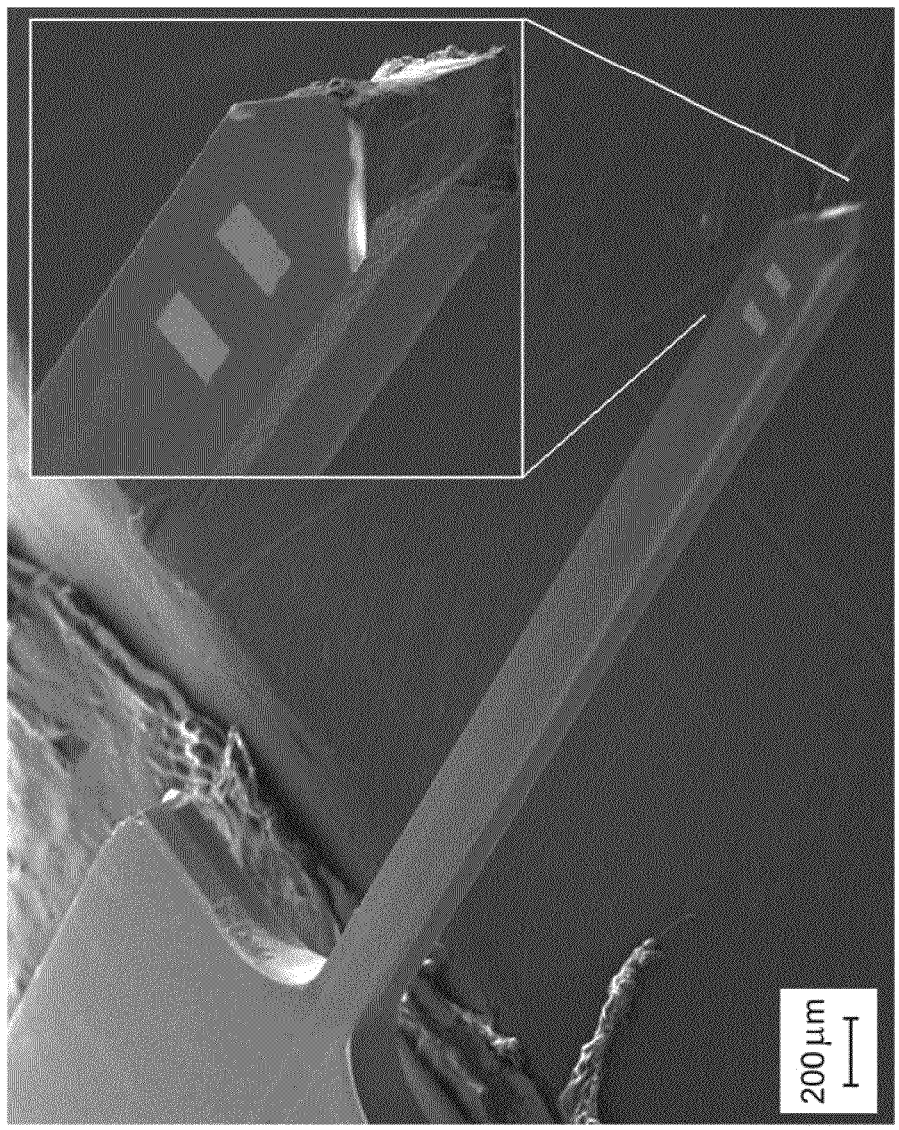

FIG. 13. SEM image of the tip of a microfabricated microcontroller-based electrical probe, with an enlargement of the ground and actuation pads. The asymmetry in obtaining the sharp tip resulted from mask asymmetry. See Examples 6.2 and 6.3.

FIGS. 14a-d. Photographs of (A) transplanted platform comprising a probe inserted in the pupa and (B) the emerged adult bearing the platform. (C) Transplanted glass capillary in the pupa and (D) the emerged adult with the glass capillary. See Examples 6.2 and 6.3.

Figure 15:
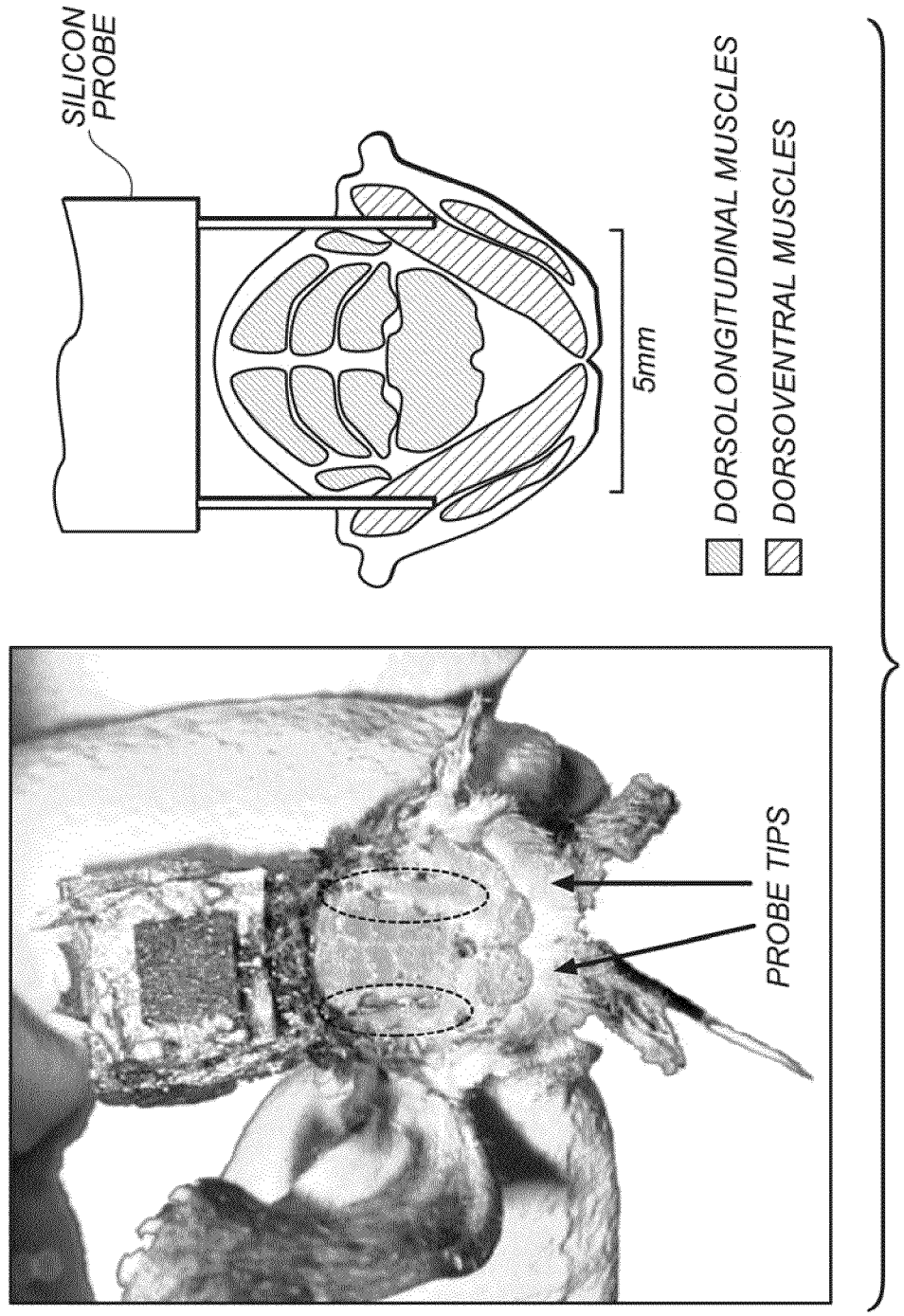

FIG. 15. Photograph of anterior transverse dissection of the thorax of an adult moth with transplanted platform (left) and schematic view of a cross-section of the thorax through the dorsolongitudinal and dorsoventral flight muscles (right). In the photograph on the left, the transplanted probes are shown with arrows and the flight muscles are encircled. See Examples 6.2 and 6.3.

Figure 16:
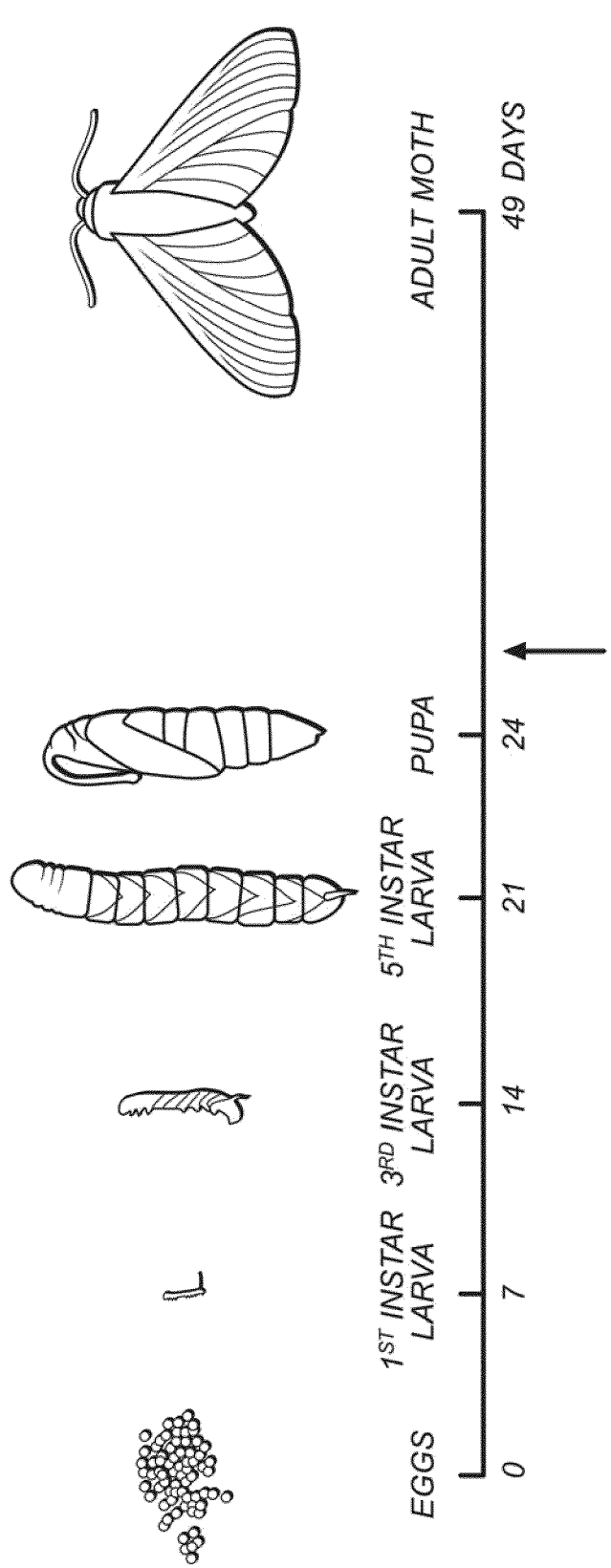

FIG. 16. Schematic of life span of a moth, indicating stage at which the microsystem and microcapillary was inserted (indicated by the arrow). See Example 6.3.

FIGS. 17a-b. (A) Experimental setup of tethered moth wing actuation using titanium wires. (B) Schematic diagram of the setup. See Example 6.3.

Figure 18:
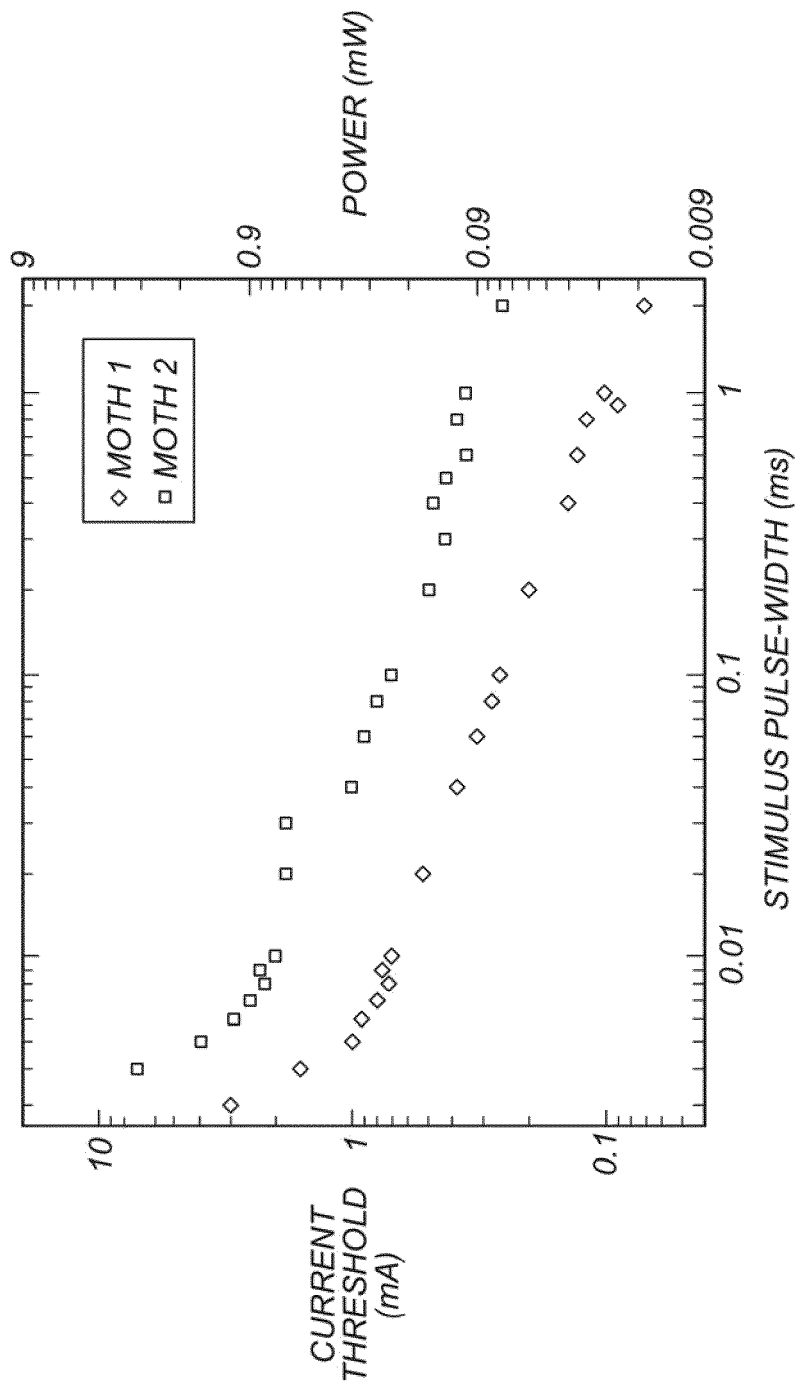

FIG. 18. Measured muscle actuation current threshold (log, mA) and power (log, mW) vs. stimulus intervals (log, ms) of two different subject moths. Moth 1 (diamonds). Moth 2 (squares). See Example 6.3.

Figure 19B:
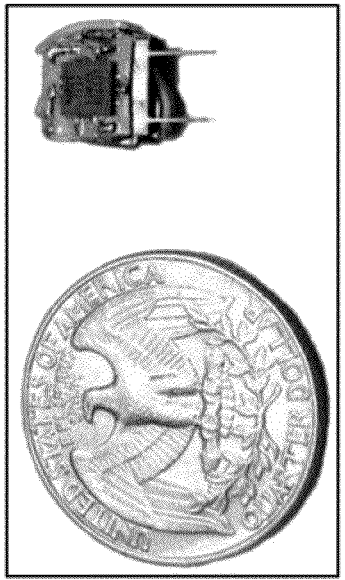
Figure 19A:
Figure 19C:
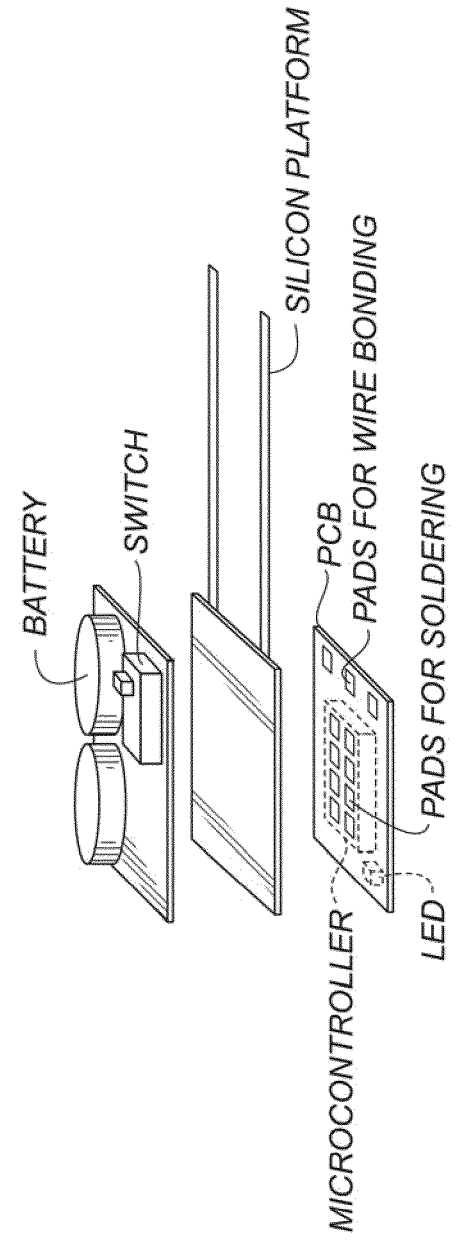

FIG. 19a-c. Assembled platforms using microfabricated probes, microcontroller and batteries. A. Front view. B. Back view. C. Schematic diagram illustrating the assembly and its components. See Example 6.3.

Figure 20:
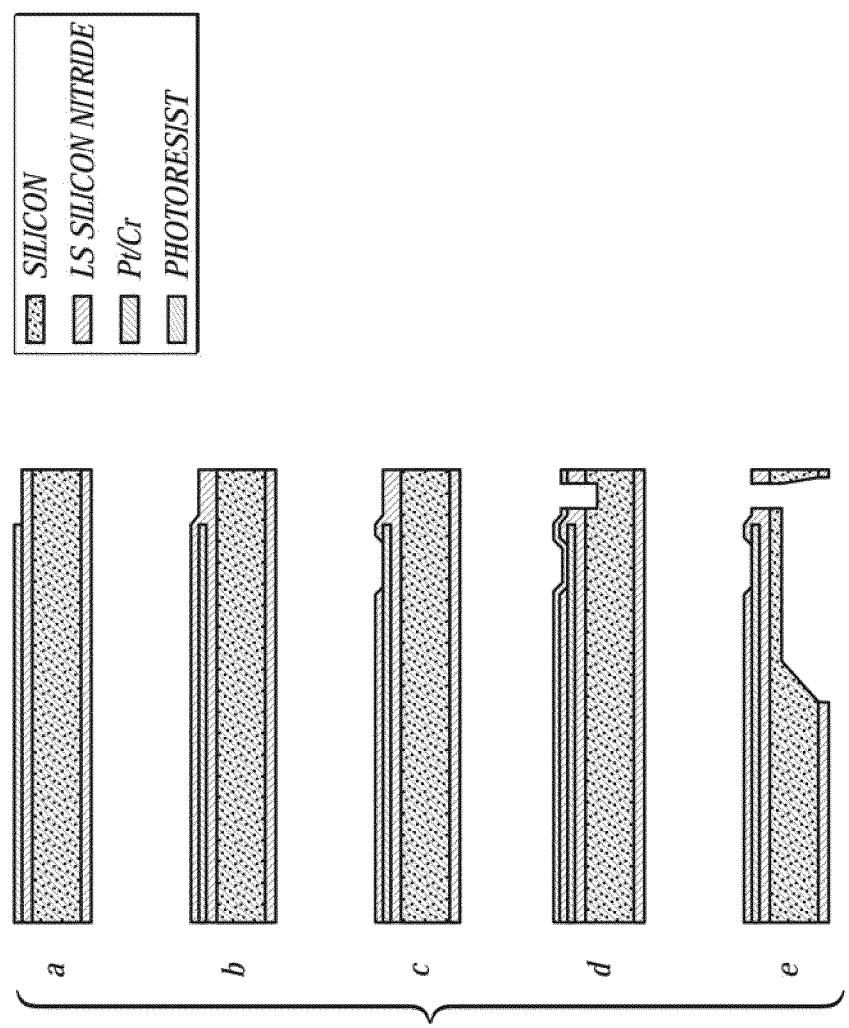

FIG. 20. Microprobe fabrication process. See Example 6.3.

FIG. 21. Time-scheme of one cycle of the flight muscle excitation algorithm. See Example 6.3.

FIG. 22. Power consumption of each component of the platform. See Example 6.3.

Figure 23B:
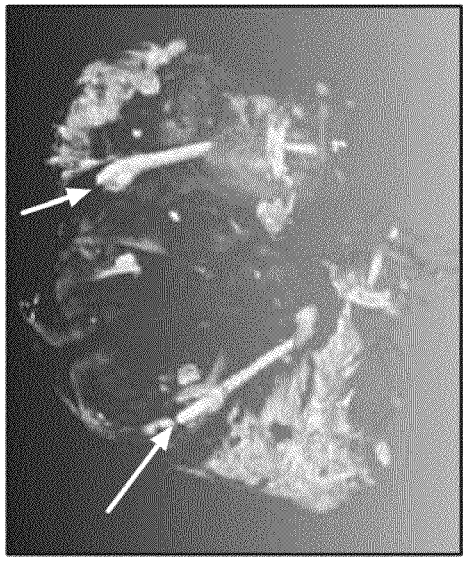
Figure 23C:
Figure 23A:
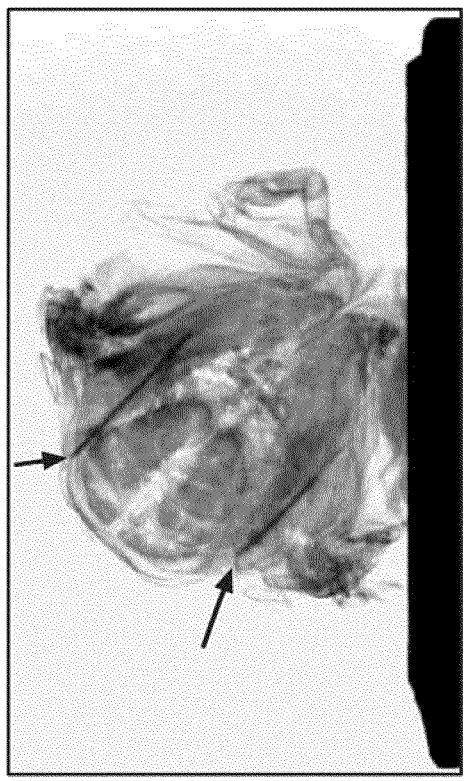

FIG. 23a-c. A. X-ray image of adult moth thorax, showing inserted silicon probes. B. Image processing of the image shown in (A), to show components of high absorbance, indicating growing tissue. C. Photograph showing the orientation of the moth in (A) and (B). Arrows indicates the inserted silicon probes. See Example 6.3.

5. DETAILED DESCRIPTION OF THE INVENTION

A method is provided for surgically implanting a microsystem into an arthropod at a developmental stage prior to adulthood, without adversely affecting the arthropod's life span, behavioral or locomotor capacity. To solve the problem associated with attaching devices to adult arthropods, the method can take advantage of the arthropod's life cycle to implant and attach (for example, permanently attach) one or more microsystems (or an attachment site or platform for a microsystem, hereinafter also referred to as a "microsystem") into an immature stage of the arthropod for eventual deployment at the adult stage.

In one embodiment, a method is provided for producing an arthropod comprising introducing a microsystem (e.g., a MEMS device or an attachment for a MEMS device) into an immature arthropod under conditions that result in production of an adult arthropod. The microsystem can be functional and attached (e.g., permanently attached) to the body of the adult arthropod.

Arthropods grow and develop by periodically molting to replace their external exoskeleton. The replacement of the exoskeleton that takes place during a molt allows for the repair of wounds that are caused by the permanent implantation of external (anchoring) devices or internal devices. A method is provided that utilizes the process of arthropod development, which involves periodic molting, to enable the implantation of a microsystem without injuring or traumatizing the arthropod. Such trauma is commonly induced by attempting to attach a microsystem or microdevice to an adult-stage arthropod.

A method is also provided for producing a robotic apparatus comprising:
introducing a microsystem into an immature arthropod (or portion thereof) under conditions that result in production of a robotic apparatus, wherein the robotic apparatus comprises:
  i. the microsystem, and
  ii. a biological system, the biological system comprising the adult arthropod (or portion thereof),
and wherein the microsystem is attached (e.g., permanently attached) to the body of the adult arthropod (or portion thereof).

A robotic apparatus or "biobot" is also provided. The robotic apparatus can comprise both a biological system and non-biological components.

A microprobe microsystem platform is also provided that comprises a power layer; a probe layer; and a control layer that can be implanted into an arthropod and can become functionally and permanently attached to the body of the adult arthropod.

For clarity of disclosure, and not by way of limitation, the detailed description of the invention is divided into the subsections set forth below.

5.1 Biological Systems

The biological system can be an intact arthropod such as an insect, crustacean or arachnid.

The biological system can also be a nearly intact arthropod that is capable of a specific motor or locomotor function associated with the arthropod's normal behavior, such as wing flapping, walking, crawling, swimming, etc.

The biological system can be capable of carrying out, or can be a functional unit for, a normal physiological function in an arthropod, such as locomotion (e.g., flying, walking, swimming), vision, hearing, chemosensation, temperature sensation, mechanoreception or pressure sensation, acceleration sensation, gravity sensation, magnetic sensation, feeding, digestion, mating and oviposition.

The biological system can comprise a portion of the adult arthropod capable of generating, regulating or controlling a specific physiological function. For example, the portion of the arthropod can be the portion of the arthropod nervous system that controls a physiological function such as locomotion, vision, hearing, chemical sensing, temperature sensing, pressure sensing, acceleration sensing, gravity sensing, magnetic sensing, feeding, digestion, oviposition, etc. In a specific embodiment, the nervous system controls, regulates or is associated with wing flapping, walking, crawling, swimming, etc. In such embodiments, the biological system may or may not comprise an arthropod appendage controlled by a portion of the nervous system.

In another embodiment, the microsystem can activate a muscle (or muscle group) that regulates the physiological function.

In another embodiment, the physiological function can be locomotion.

In another embodiment, the muscle (or muscle group) can be flight muscle and the locomotion can be flying.

In another embodiment, the muscle (or muscle group) can be leg muscle and the locomotion can be walking.

In one embodiment, the arthropod can be a holometabolous (metamorphic) insect, which has four distinct life stages: egg, larva, pupa (imago) and adult (FIGS. 1, 9 and 16), such as Lepidopeterans (butterflies or moths), Dipterans (flies), or beetles. In a specific embodiment, the insect can be the hawkmoth (or tobacco hornworm moth), *Manduca sexta*.

In another embodiment, the arthropod can be a hemimetabolous insect, i.e., an insect that goes through a series of nymphal stages prior to the adult stage, such as a cockroach or grasshopper.

The aerodynamic performance of insects is superior to existing flying machines. A method is provided by which a flying insect can be surgically modified to produce a highly efficient MAV. Some large insects, such as certain species of butterflies and moths, have powerful flight muscles. Using the method provided, such insects can be equipped to carry a microsystem (e.g., a MEMS device, a telemetric device). In one embodiment, the microsystem can weigh 0.001-1.0 g. In another embodiment, the microsystem can weigh 1-5 g. In another embodiment, the microsystem can weigh 5-10 g. In another embodiment, the microsystem can weigh at least 10 g.

5.2. Introduction of Foreign Objects into Arthropods

Methods are provided for introducing a biocompatible foreign object into an arthropod at a stage of its developmental cycle prior to the adult stage. The biocompatible foreign object can a microsystem (see Section 5.3 below).

By introducing the biocompatible object into the arthropod during post-embryonic development and prior to adulthood, one can take advantage of the self-healing and tissue restructuring that occurs during postembryonic development to form reliable electromechanical interfaces to the arthropod body. After the adult emerges or fully develops, the microsystem is perceived as natural weight and the arthropod's behavior is not greatly altered.

A method is provided for introducing a microsystem (or a substrate for the attachment of a microsystem) into an arthropod by surgical implantation. According to this method, such surgical implantation does not adversely affect the arthropod's adult lifespan. As well known in the art, arthropods, including insects, crustaceans and arachnids, can survive extreme surgery (e.g., parabiosis, decapitation, isolated development of imaginal disks within a host) and methods for such surgeries are well known in the art (see, e.g., Williams, C. M. 1946. Physiology of insect diapause: the role of the brain in the production and termination of pupal dormancy in the giant silkworm *Platysemia cecropia*. Biol. Bull. Mar. biol. Lab., Woods Hole 90:234-243; Williams, C. M. 1952. Physiology of insect diapause. IV. The brain and prothoracic glands as an endocrine system in the Cecropia silkworm. Biol. Bull. Mar. biol. Lab., Woods Hole 103: 120-38; Ephrussi, B. and Beadle, G. W. 1936. A technique of transplantation for *Drosophila*. Am. Nat. 70, 218-25).

In one embodiment, a substrate, microplatform, or microsystem can be surgically implanted prior to the adult stage of the arthropod during a larval, nymphal stage or other pre-adult stage, subsequent to hatching from the egg but prior to the adult stage.

In another embodiment, a microsystem can be surgically implanted in a holometabolous insect during a larval stage or a pupal stage of post-embryonic development or metamorphosis (FIG. 1). In a one embodiment, surgical implantation of the microsystem can be performed in a pupal stage, when the pupa is immobile.

In a preferred embodiment, a microsystem can be introduced into a late-stage pupa or other late developmental stage of the arthropod. Introduction at the late pupal stage usually results in higher survival and rate of adult emergence.

In a specific embodiment, a microsystem can be introduced into a moth pupa one day before emergence.

Implantation of a microsystem during the pre-adult stage (e.g., during the larval or pupal stages, during nymphal development) does not adversely affect the insect's survival or normal locomotory capability (e.g., flying, walking, swimming). The provided method can be used to produce a "biobot" or robotic apparatus comprising biological tissue (e.g., an entire insect or portions thereof) and one or more non-biological components (e.g., a MEMS device). Such a robotic apparatus can be adapted for a variety of applications (see Section 5.4 below).

According to the provided method, a foreign object such as a microsystem can be inserted in a region of the arthropod body in which it will not interfere with normal development of the adult structures. In one embodiment, the foreign object can be inserted into the abdomen. Abdominal implantation is preferable since the inserted object does not interfere with proper leg and wing formation occurring in the thorax during metamorphosis or post-embryonic development.

In another embodiment, the foreign object can be inserted into the head or thorax of the arthropod, preferably in a region that will not impede the development or eversion of adult structures such as eyes, appendages (e.g., antennae, wings, or legs), etc.

In another embodiment, an "attachment-type" microsystem, e.g., a silk thread insert, silicon insert, or a titanium wire, can be introduced into a larva (e.g., late instar larva), nymph, or pupa.

According to the method, the inserted microsystem (or any tether, attachment point, substrate or platform for an attached microsystem, which are also referred to herein as a microsystem) can be permanently and securely anchored onto the arthropod's body because its tissues grow, surround and attach to the microsystem during development. This growth, however, does not interfere with the normal functioning or performance of the microsystem.

Since in certain embodiments, the insertion of the microsystem can be performed on an immobile stage of arthropod development, the method can be used for the mass production of arthropods with surgically implanted Microsystems. Furthermore, permanent attachment of the microsystem can ensure secure delivery of the microsystem to a target site.

In one embodiment, arthropods at a pupal, nymphal or other pre-adult stage can be prepared for surgery as follows. The surgery can be performed on arthropods that are preferably anesthetized, for example, by chilling on ice (cold anesthesia). The cuticle is removed from the section of the body where the microsystem is to be inserted.

In a specific embodiment, a micro-cargo platform can be implanted in an arthropod that is constructed of two biocompatible titanium wires (0.01" diameter, 0.25" length) and a 0.2"×0.2" balsa wood platform (FIGS. 2a-d and 4a-d). Such a platform can be inserted into the dorsal abdominal cavity of a pupa (FIGS. 2b-d) at the point where the cuticle removed.

In another embodiment, a silicon chip can be implanted. FIGS. 3a-d and 5a-d show a specific embodiment in which a 2 mm×4 mm×0.5 µm silicon chip was inserted in the ventral abdominal cavity of a pupa at the point where the cuticle is removed.

In another embodiment, a silk thread can be implanted, which forms an attachment point for another microsystem (FIGS. 6a-d). A curved surgical needle threaded with silk thread can be used, for example, to make a suture on the dorsal abdominal cuticle in an immature or adult stage of the arthropod.

In another embodiment, one or more titanium or other biocompatible wires can be inserted at a pre-adult stage of arthropod development into the posterior end of the abdomen up into the thorax, and run the whole length of the abdomen to the thorax. According to this embodiment, a microsystem can be subsequently integrated into the body.

In a specific embodiment, the wire can be inserted at an early pupal stage through the posterior end of the abdomen, and can run the whole length of the abdomen to the thorax (FIG. 7a-c). According to this embodiment, a microsystem can be subsequently integrated into the body of the arthropod. In this embodiment, however, the arthropods undergoing implantation generally exhibit lower rates of survival than any of the above-mentioned inserts.

After surgery is completed, the arthropods can be kept under conditions well known in the art that promote development, e.g., maintained in an incubator, until they metamorphose, develop, emerge or molt into adults.

5.3. Microsystems

A method is provided for introducing a biocompatible foreign object into the body of an arthropod at an immature stage, under conditions that allow it to be permanently anchored to the body of the adult insect once the insect matures and metamorphoses (e.g., holometabolous insect) or molts (e.g., hemimetabolous insect, crustacean, arachnid) into the adult stage. In one embodiment, the biocompatible foreign object can be a microsystem.

An apparatus is also provided comprising a non-biologically derived microsystem and a biological system.

Biocompatible materials are materials that are designed to exist and perform specific functions within living organisms. These include a broad range of substances such as structural metallic orthopedic prosthetic implants, artificial blood and skin, and surface coatings for implantable sensors for chronic (long-term) monitoring or electrodes for functional electrical stimulation. In arthropods, biocompatible materials include, but are not limited to, silicon, silk, titanium, microcapillary tubes, micro-nano beads and hydrogels.

Methods for determining biocompatibility of a foreign object in arthropods are well known in the art. While implant durability is one concern, another concern is the body's ability to reject these materials as foreign objects either through an adverse immune system response or by attempting to "wall them off" by surrounding them with a protein layer. Arthropods have limited immune and "walling off" responses (when compared with vertebrates such as mammals), and are well known in the art to exhibit a far greater tolerance for implantation of a foreign object.

In one embodiment, the microsystem can be an attachment apparatus such as a thread, wire, tether, loop, post, screw or hook. The attachment point can be composed of any biocompatible material known in the art, e.g., titanium, silk, silicon, microcapillary tubes, micro-nano beads and hydrogels. In specific embodiments, the attachment apparatus can be a titanium wire or a silk thread.

In another embodiment, the microsystem can be an attachment substrate or microplatform, to which one or more additional microsystems or "micro-cargoes" can be added or attached. In a specific embodiment, the substrate can be a microplatform for a microelectromechanical system (MEMS) device.

In another embodiment, the microsystem can be a MEMS device, which can include, but is not limited to, a meso-sized device having feature sizes between 500 mm and 2 mm, a micro-sized device having feature sizes between 500 nm and 500 mm, and a nano-sized device having feature sizes between 1 nm and 500 nm. The MEMS device can be any MEMS device known in the art, for example, an accelerometer, gyroscope, temperature sensor, chemical sensor, electrophysiological stimulator, micro-lens, comb-drive actuator, or piezoelectric actuator.

A microprobe microsystem platform is also provided that can comprise a power layer; a layer comprising a probe ("probe layer"); and a control layer (see, e.g., FIGS. 11a-c and 19a-c).

In one embodiment, the power layer can comprise a power source and a switch.

In another embodiment, the power source can be a battery.

In another embodiment, the power layer can comprise a printed circuit board (PCB).

In another embodiment, the control layer can comprise a microcontroller (or meso-, micro- or nano-scale controller).

In another embodiment, the control layer can comprise a PCB and a microcontroller functionally connected to the PCB.

In another embodiment, the control layer can comprise an LED.

In another embodiment, the probe layer can comprise a probe that is a microfabricated silicon probe.

In another embodiment, the probe layer can be positioned between the control layer and the power layer.

In another embodiment, the probe can comprise a plurality of tips, wherein a member of the plurality can be separated from a second member of the plurality by a distance that corresponds to the distance between two cells, tissues or physiological systems of interest.

In another embodiment, the two physiological systems can be two muscles (or muscle groups). In a specific embodiment, the muscles can be flight muscles. In another specific embodiment, the muscles can be leg muscles.

In another embodiment, the two physiological systems can be two neurons (or neural systems, neural centers, or ganglia).

In another embodiment, the probe can be activated by an algorithm whereby sequential electrical pulses are sent to the probe tip(s).

In another embodiment, the LED on the control layer can be used to monitor electrical excitation generated by the probe.

5.4. Robotic Apparatus

A robotic apparatus or "biobot" is also provided. The robotic apparatus can comprise biological tissue (e.g., an arthropod or portion thereof) and one or more non-biological components. In one embodiment, the apparatus can comprise a microsystem and a biological system. The biological system can comprise an adult arthropod (or portion thereof). The microsystem can be permanently attached to the body of the adult arthropod (or portion thereof).

In another embodiment, the apparatus can be an intact (or nearly intact) biological system incorporated into the design of a microsystem (e.g., a MEMS device). In another embodiment, the apparatus can comprise a portion of a biological system incorporated into the design of the microsystem. For example, a biological interface can be created between the inserted microsystem and e.g., cell, tissues or physiological systems of the arthropod, e.g., muscle tissue or neural tissue that controls a specific behavior or physiological function. In a specific embodiment, the biological interface can be between insect flight muscle and the inserted microsystem. In another specific embodiment, the interface can be between insect leg muscle and the inserted microsystem.

In another embodiment, the apparatus can be a micro aerial vehicle (MAV) or unmanned aerial vehicle (UAV) comprising an adult arthropod (or a functional or partially functional portion thereof) and a permanently attached microsystem, e.g., a mm-scale low power microsystem, such as a MEMS sensor or actuator.

Since, according to the provided method, the implantation of a non-biological component, e.g., a microdevice, can be performed in the earlier stages of the arthropod's development (e.g., in the pupa during post-embryonic metamorphosis, during a nymphal stage, during a larval stage), the adult arthropod can have enhanced capacity to carry a useful payload, e.g. a microsystem such as a sensor or an actuator.

In one embodiment, the robotic apparatus can be constructed according to the provided method, wherein the method can comprise:

a. introducing a microsystem into an immature arthropod (or portion thereof) under conditions that result in production of a robotic apparatus,
wherein the robotic apparatus can comprise:
i. the microsystem, and
ii. a biological system, wherein the biological system can comprise the adult arthropod (or portion thereof),
and wherein the microsystem can be attached (e.g., permanently attached) to the body of the adult arthropod (or portion thereof).

In one embodiment, the biological system can comprise a portion of the adult arthropod capable of generating or controlling a physiological function of the adult arthropod. The robotic apparatus can be capable of carrying out the physiological function (or a portion or subfunction of the physiological function).

In another embodiment, the physiological function can be selected from the group consisting of locomotion, vision, hearing, chemosensation, temperature sensation, mechanoreception or pressure sensation, acceleration sensation, gravity sensation, magnetic sensation, feeding, digestion, mating and oviposition.

In another embodiment, the provided apparatus can be employed to monitor arthropod migration or dispersion, for example, locust migration, butterfly migration, biocontrol agent e.g. weevil migration, or lobster migration.

In another embodiment, the apparatus can be employed for environmental monitoring, e.g., atmospheric conditions, air quality, or water quality. Flying arthropods such as Lepidoptera or Diptera are particularly well suited for use as the biological system in the apparatus, e.g., for monitoring air or atmospheric conditions. Aquatic arthropods such as crustaceans or aquatic beetles are particularly well suited for use as the biological system in the apparatus for monitoring water conditions.

In another embodiment, the apparatus can be used as a source of energy that can be harvested using routine methods known in the art. Energy sources provided by the apparatus that can be harvested are, for example: (a) internal heat that is generated during flight, walking, swimming or other forms of arthropod locomotion, (b) mechanical energy of locomotion, such as wing beat frequency during flight or swimmeret frequency during swimming, that can be harvested, e.g., by applying the mechanical stress or deformation generated by the locomotion onto piezoelectric crystals, and (c) energy harvested from reserve fat bodies and ATP pumps, thereby using these energy resources from the insect to derive power.

In another embodiment, the apparatus can be used as a cognitive or behavioral interface. For example, an implanted microsystem that has a neural, muscular, or neuromuscular interface can be used to control intrinsic arthropod behavior. Implanted Microsystems can be used in the brain or in muscles that control the movement of appendages (such as wings or legs) to enable better control of arthropods during locomotion.

6. EXAMPLES

6.1. Example 1

Surgically Implanted Micro-Platforms in the Moth, *Manduca sexta*, at Intermediate Stages of Metamorphosis

6.1.1. Introduction

This example demonstrates the surgical implantation of biocompatible platforms and substrates for attachment of microsystems in insects without adverse effect to adult lifespan. According to the methods set forth in this example, a biocompatible balsa-titanium anchor was inserted in the late pupal stage of the hawkmoth, *Manduca sexta*, resulting in a permanently anchored base in the adult. Silicon chips were inserted in the late pupal stage. The inserted substrates became permanently incorporated into the resulting adult moth as the wound healed and the anchor site reinforced during the process of metamorphosis. This technology opens up a wide venue for development of microsystems or microdevices (e.g., MEMS devices) that can be attached on or inserted into insects. Modified insects can be used, for example, as hybrid systems for generating telemetric units to study biomonitoring, insect migration and dispersion patterns and various other applications.

6.1.2. Materials and Methods

*Manduca sexta* larvae and pupae (Carolina Biological Supply Company, Burlington, N.C.) were reared at 26° C., with 80% relative humidity and a 12:12 h light:dark photoperiod. Upon emergence, adult moths were transferred to a 1 m×0.5 m wire cage, which provided perches for proper expansion of the wings.

Prior to surgery, fifth (last) instar larvae, pupae, and adult moths were chilled on ice for 10 minutes. Microsystems that were attachment systems, i.e., loops of surgical braided silk surgical sutures (Fine Science Tool, Foster City, Calif.)

(FIGS. 6a-d) or biocompatible titanium wire posts 0.01 inch diameter (Small Parts Inc., Miami Lakes, Fla.) were threaded through the insect's abdomen (in the case of larvae) and dorsal thorax (in the case of pupae and adults). In the larva, the wound was sealed by applying a small drop of melted dental wax.

The titanium anchors were looped through a 5×3 mm balsa wood block to create a platform on the outside of the insect to which a microsystem or weight could then be securely attached (FIGS. 2a-d).

For insertion of a silicon chip (4 mm×2 mm×0.5 mm), the late pupal stage or the adult stage was chosen. To insert the chip, an incision was made along the body wall of the ventral side of the abdomen and the chip was inserted into the body cavity. The wound was then sealed with dental wax (FIGS. 3a-d).

A circuit board with a miniature LED-based device to regulate direction of flight in the adult moth was also constructed according to routine methods. (FIG. 8).

Control larvae, pupae and adults were subjected to chilling (cold anesthesia) only and were not subjected to surgery. The insects were then housed individually to reduce the chances of contamination or infection. Larvae took 20 days, and the late pupae 24 to 48 hours, to complete metamorphosis and emerge as adults. The operated and the control moths were observed for differences in the number of days each required for emergence and their survival time period as adults. FIGS. 5a-d show the results of the implantation of a 2 mm×4 mm×0.5 µm silicon chip into the ventral abdominal cavity of a pupa.

6.1.3. Results

The survival rates of insects bearing silk or titanium loops that were inserted at the late larval, pupal (early and late pupae) or adult stage were first evaluated (Table 2). Larvae with silk loops inserted longitudinally (LS) showed higher survival rates than did larvae with loops inserted transversally (CS) as the latter insertion often punctured the foregut of the larvae. Individuals with silk tethers inserted at the pupal stage showed the same emergence time as the control unaltered pupae. Both the pupae and the adults with inserted silk tethers showed normal survival rates when compared to controls (Table 2). Larvae with titanium wire posts did not survive the surgery and failed to molt into a pupa, most likely because the rigid structure of the wire prevented normal metamorphosis.

Late pupae and adults bearing titanium wire loops and balsa wood micro-cargo platforms showed survival rates of 100% and 93%, respectively (N=30 and N=15 for pupae and adults, respectively) (Table 2).

TABLE 2

Survival rates of *Manduca sexta* with insertions made at different stages of its life cycle

| Implanted Structure | Implanting life stage | Number implanted | Number surviving with inserts at developmental stage | | | % survival |
|---|---|---|---|---|---|---|
| | | | Larva[a] | Pupa[b] | Adult[c] | |
| Silk thread (CS insert) | Larvae | 20 | 0 | 0 | 0 | 0 |
| | Pupae | 10 | — | 8 | 8 | 80 |
| | Adult | 5 | — | — | 5 | 100 |
| Silk thread (LS insert) | Larvae | 20 | 19 | 18 | 18 | 90 |
| | Pupae | 10 | — | 10 | 9 | 90 |
| | Adult | 5 | — | — | 5 | 100 |
| Titanium Wire | Larvae | 10 | 0 | 0 | 0 | 0 |
| | Pupae | 30 | — | 30 | 30 | 100 |
| | Adult | 15 | — | — | 14 | 93.33 |

TABLE 2-continued

Survival rates of *Manduca sexta* with insertions made at different stages of its life cycle

| Implanted Structure | Implanting life stage | Number implanted | Number surviving with inserts at developmental stage | | | % survival |
|---|---|---|---|---|---|---|
| | | | Larva[a] | Pupa[b] | Adult[c] | |
| Silicon chip | Larvae | 5 | 0 | 0 | 0 | 0 |
| | Pupae | 15 | — | 12 | 7 | 80 |
| | Adult | 15 | — | — | 10 | 66.6 |
| Total = 153 | | | | | | |

Figure 4B:
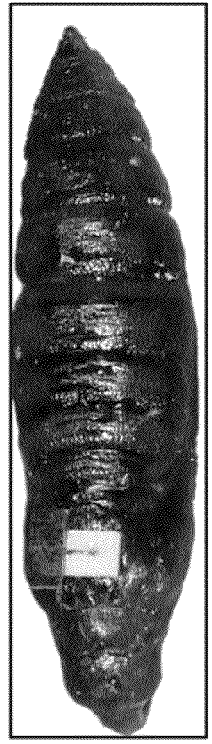
Figure 4D:
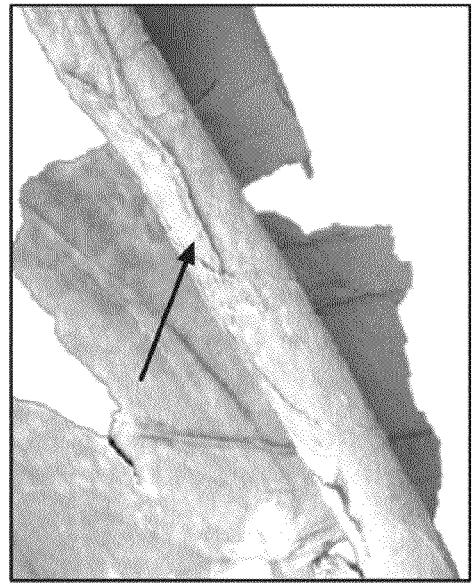
Figure 4A:
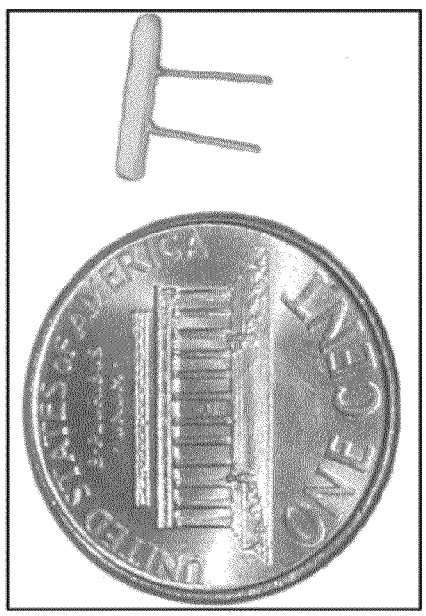
Figure 4C:
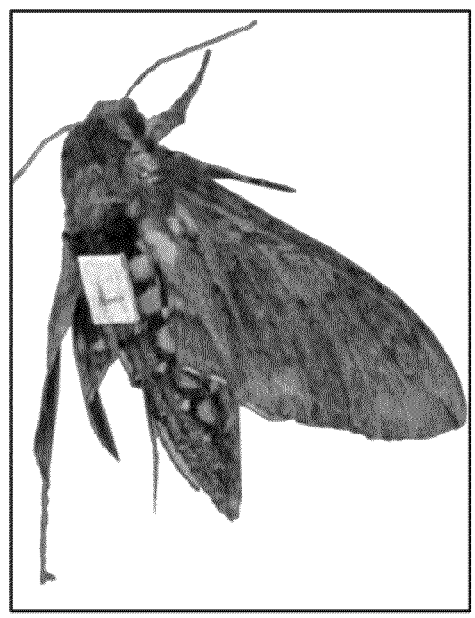
Figure 5B:
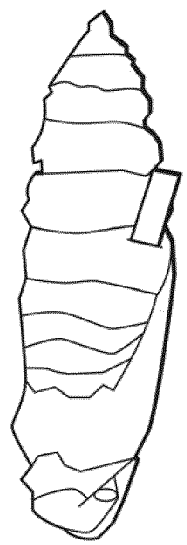
Figure 5D:
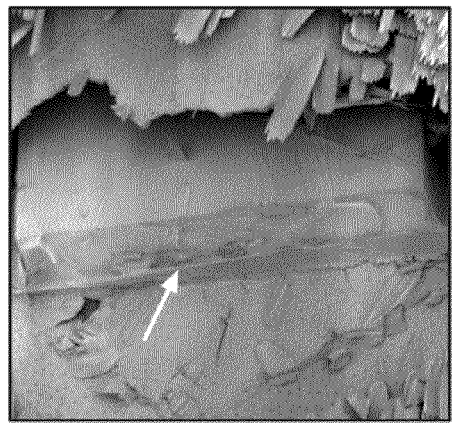
Figure 5A:
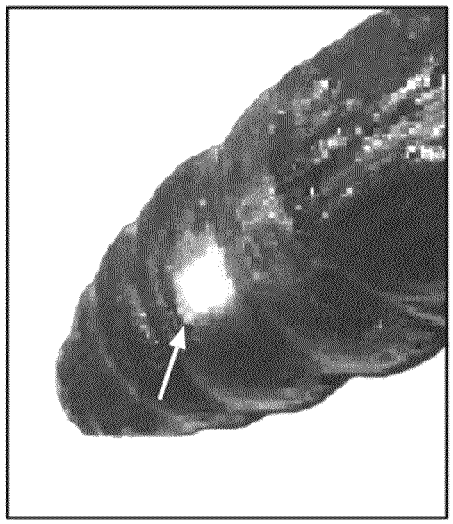
Figure 5C:
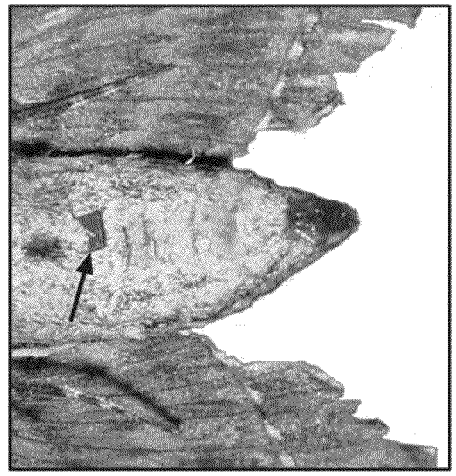
Figure 6B:
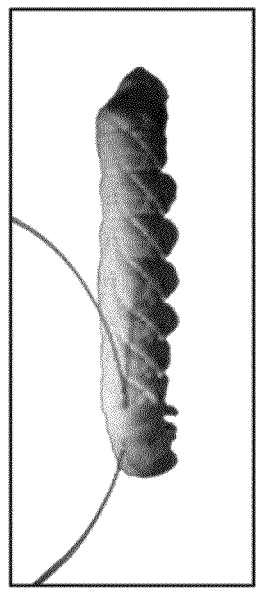
Figure 6D:
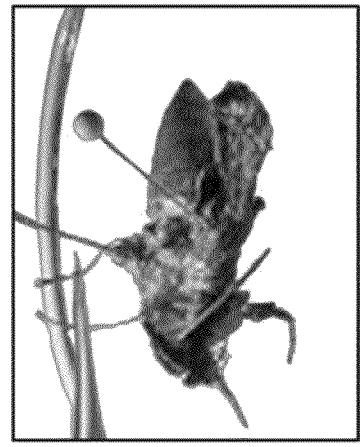
Figure 6A:
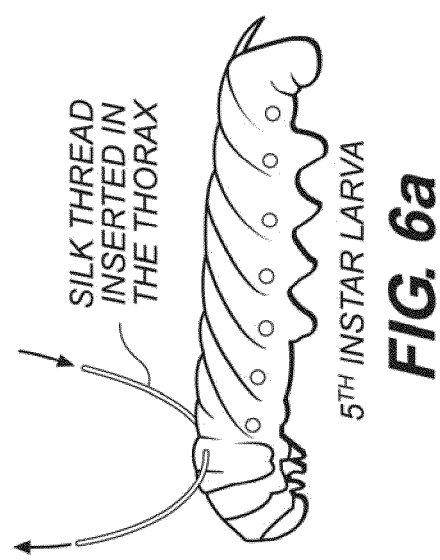
Figure 6C:
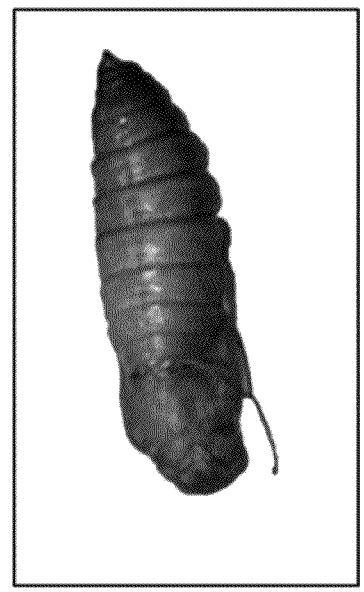

[a]Survival to the adult when insertion was made at the late larval stage
[b]Survival to the adult when insertion was made at the late pupal stage
[c]Survival of adults 48 h after insertion was made at the adult stage Inspection via scanning electron microscopy (SEM) of the titanium wire (inserted in the late pupal stage) two days after adult emergence revealed that there was tissue growth around the wire posts (FIG. 4d).

The survival rates of moths bearing a silicon chip were also evaluated. Moths bearing chips inserted at the late pupal stage showed 80% survival and emergence as adults (N=15) (FIG. 3a-d). When the insertion was made at the adult stage (1 day old) the survival rate was 67%. (N=15).

Figure 3A:
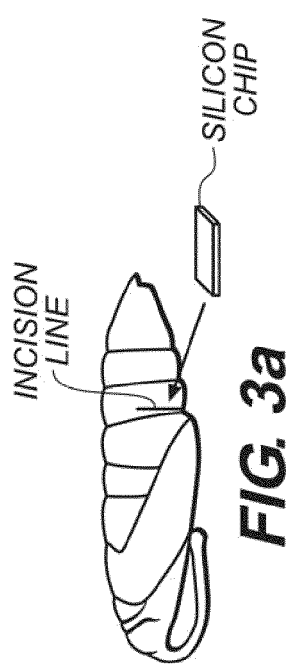
Figure 3D:
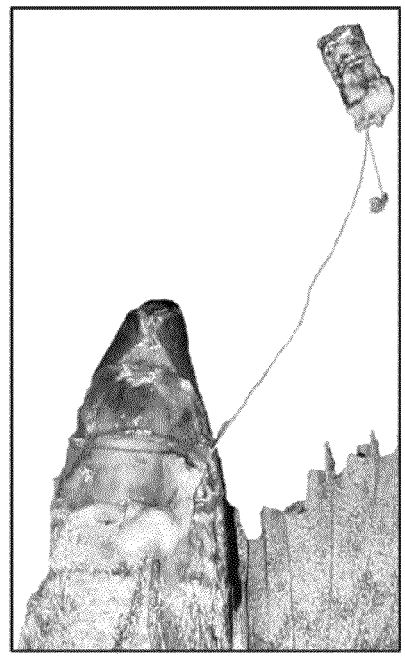
Figure 3C:
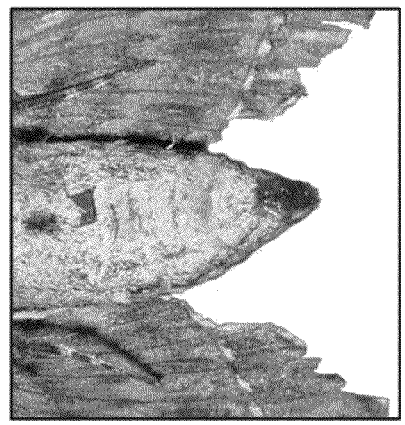
Figure 3B:
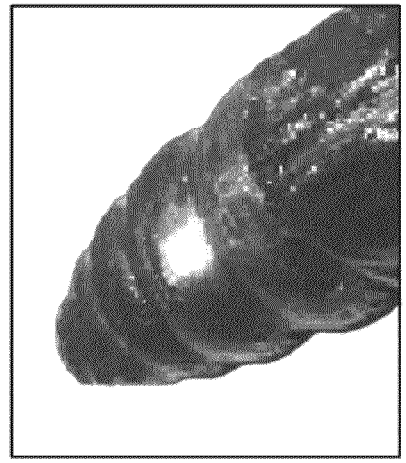

Integration of the silicon chip within the abdominal cavity was demonstrated by tissue loss while prying the insert out of the body cavity of the adult. This was due to tissue growth to, and attachment around, the silicon chip (FIG. 3d).

6.1.4. Discussion

The results obtained indicate that an insect can be utilized to carry Microsystems, either tethered to its body or inserted within its body cavity. Insertion of silicon chips in the body cavity opens up a venue for formulating and manufacturing microdevices that can be incorporated into arthropods.

Inserting devices during the pupal stage did not significantly affect the insect's survival to the adult stage, and had the advantage that the wounds caused by surgery healed during the process of molting and the tanning (hardening) that took place after emergence. In addition, the tissue that appeared to grow around the insert yielded a more reliable bio-microsystem interface between the insect and the insert.

Thus, implantation of microsystems during immature stages prior to adulthood overcomes the difficulties encountered when attempting to attach such devices in an adult arthropod. Insertion of devices/platforms at the relatively immobile metamorphic stage is also advantageous for the mass production of these hybrid or "biobot" systems comprising both biological tissue and non-biological components.

The technology demonstrated here confirms that substrates or platforms for Microsystems such as MEMS sensors and actuators can be implanted at various post-hatching, post-embryonic or metamorphic stages in an arthropods lifecycle prior to adulthood. The $cm^3$ scale microsystems of many MEMS devices known in the art are well suited for implantation into the cm-dimensions of large flying insects such as a Lepidoptera.

Furthermore, if a platform is inserted and the load attached during an immature stage, the foreign load can be perceived by the insect as part of its body weight upon emergence. This results in higher payload carrying capacity of the insect and/or greater flight activity, compared to insects in which tethers are attached in the adult. Moreover, modifying the duration of development, e.g., post-embryonic or metamorphic development, by modifying temperature and/or other environmental or hormonal stimuli, can enable the production of adults at a desired time. Finally, the tissue growth around the microsystem in the insect body presents a bio-electromechanical interface that can be used to study various physiological responses of the insect to external stimuli that control locomotion or flight.

Additionally, the tissue growth around the Microsystems in the insect body presents a bio-electromechanical interface that can be used to control locomotion by stimulating nerves and/or muscles to bias insect behavior such as flight. Locomotion can also be controlled by manipulating the sensory organs with external stimuli such as ultrasound, pheromones, and light wavelength and patterns. These external stimuli, if generated by a MEMS-sized actuator, can be positioned on or in the insect. This can override the insect's instinctive behavior and result in more accurate control of its locomotion towards a target.

6.2. Example 2

Biocompatible Microfabricated Probe Platform Inserted During Metamorphosis to Actuate Insect Flight Muscle

6.2.1. Introduction

This example demonstrates the surgical implantation of a biocompatible, microfabricated microcontroller-based electrical probe for the actuation of flight muscle in the hawkmoth, *Manduca sexta*.

Many species of insects, including moths, have two sets of flight muscles that are present on either side of the thorax (Eaton, J. L. 1971. Morphology of the head and thorax of the adult tobacco hornworm, *Manduca sexta* (Lepidoptera: Sphingidae). I. Skeleton and muscles. Ann. ent. Soc. Am. 64: 437-445). These two sets of flight muscles are differentially actuated by voltage pulses that directly influence the individual wing beat frequency and amplitude, hence resulting in turning behavior during flight. As demonstrated in the previous example (Section 6.1, Example 1) insects survive insertion of foreign objects, such as silicon chips and titanium wires, during metamorphosis, and incorporate the inserted foreign object into the body by tissue growth around it (see also, Paul, A., Bozkurt, A., Ewer, J., Blossey, B. and Lal, A. 2006. Surgically Implanted Micro-Platforms in *Manduca sexta*, 2006 Solid State Sensor and Actuator Workshop, Hilton Head Island, June 2006, pp 209-211.)

6.2.2. Materials and Methods

In the first set of experiments, flight muscles were actuated by inserting titanium wires in the thorax of a tethered moth and using a current to stimulate the flight muscles.

A silicon-chip based probe system was then created to actuate the flight muscles autonomously in an untethered insect. This microsystem had batteries on it to provide electrical stimuli to the flight muscles. Microprobes designed to actuate flight muscles were constructed using routine methods known in the art The microprobes (FIGS. 11*a-c*, 12, 13) were inserted, using insect surgical methods commonly known in the art, into the thorax of the metamorphosing moth during the early pupal stage (FIGS. 9 and 14*a-d*).

Titanium wires were inserted into the dorsoventral flight muscles in the thorax using routine surgical methods. The titanium wires were used to initiate artificial wing flapping Current pulses of different pulse-widths were applied to the muscle fibers using routine electrophysiological methods. (FIG. 10).

An 8×13 mm$^2$, 0.5 g stand-alone platform was constructed, according to standard methods known in the art, to apply controlled voltage pulses to the flight muscles. The platform consisted of three layers: power, probe and control layers (FIGS. 11*a-c* and 12). The power layer was formed by two serially connected 1.5V SR416SW-type batteries and a slide-switch. The control layer comprised an 8×8 mm$^2$ PCB holding the microcontroller (Atmel Tiny13V) and an LED. The probe layer was a microfabricated silicon probe sandwiched between these two layers and had a thickness and width of 200 μm at the tip (FIG. 12). The micro-platform with probes for stimulating the muscles was thus a self-contained unit fabricated onto the silicon chip.

FIG. 12 shows a schematic diagram of the fabrication process of the microfabricated microcontroller-based electrical probe, which was fabricated according to routine methods in the art.

Distance between the two probe tips was 5 mm and was equal to the distance between the right and left flight muscles of the moth. The metal lines that actuate these muscle cells were only exposed close the end of the tip to avoid any short contact (FIG. 13). Electrical contact between layers was provided by wire-bonding and soldering.

The micro-platform was inserted on the thorax using the surgical methods described herein after the first quarter of the pupal stage (typically 15 days long), when the pupal cuticle became hard. A glass capillary with a diameter of 250 microns, which served as a microfluidic port, was inserted into the posterior end of the pupa and extended into the thorax of the pupa (FIG. 14*c*).

When the switch was turned on, the microcontroller sent sequential 3V voltage pulses with a frequency of 30 Hz (natural wing-beat frequency) to the right and left tips of the probe. To elicit differential wing actuation, the right flight muscle was actuated for 5 seconds, which was then followed by a 10 seconds idle period. After this, left muscle was actuated for 5 seconds with a consecutive 40 seconds idle period to avoid habituation. This was repeated until the switch on the power layer was turned off. To indicate the onset of each actuation, an LED blink was programmed, using routine methods, into the microcontroller.

6.2.3. Results and Discussion

Current pulses applied to the muscle fibers set up a propagated action potential, which lead to the initiation of a twitch contraction. Current pulses with different pulse-widths were applied and current amplitude to initiate the flapping was measured (FIG. 10). Differential excitation of left and right muscle groups was also observed (data not shown).

Figure 14D:
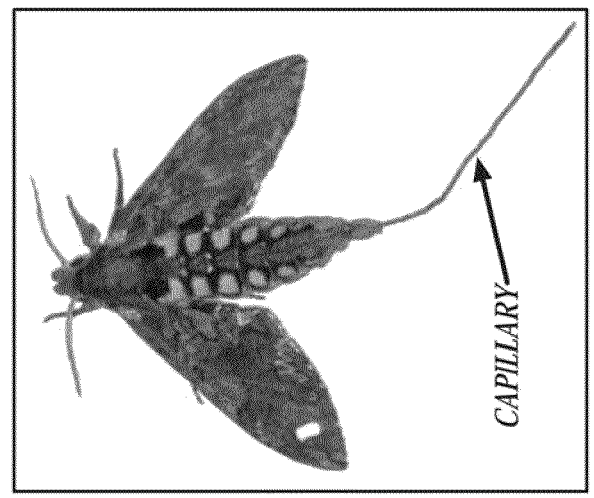
Figure 14C:
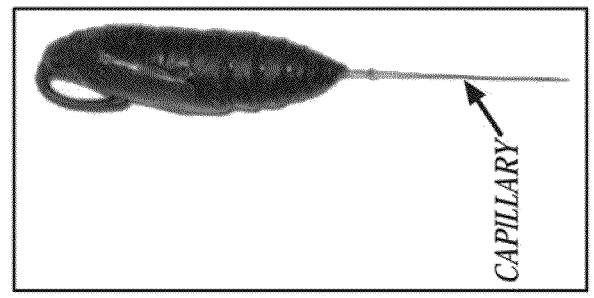
Figure 14A:
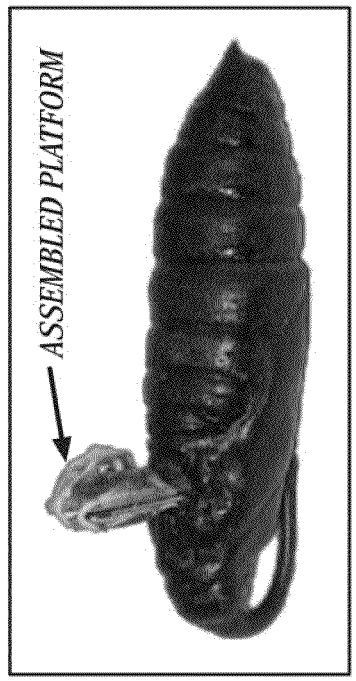
Figure 14B:
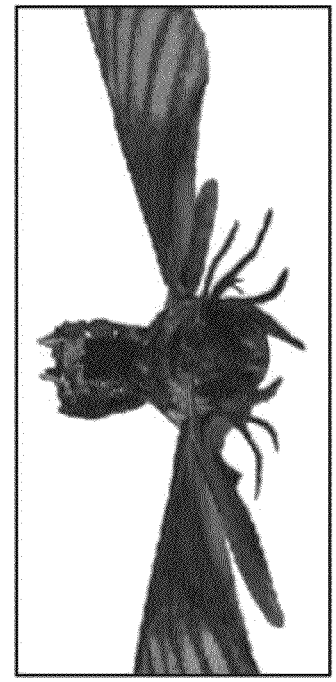

The pupae survived the surgical implantations and emerged as full grown adults (FIGS. 14*b*, 14*d*, 15). Most pupae emerged normally as adults, although in some cases, they were unable to inflate and spread their wings. Dissections of the thorax were performed to observe the results and efficiency of the insertion (FIG. 15).

6.3. Example 3

Microprobe Microsystem Platform Inserted During Early Metamorphosis to Actuate Insect Flight Muscle

6.3.1. Abstract

This example demonstrates the construction of a microprobe-based microsystem platform, which was designed with respect to the position of the flight muscles in a moth, *Manduca sexta*. The platform was roughly 8×7×1.5 mm3 in size with probe thickness of 200 μm, and weighed 500 mg. The platform was inserted into the thorax at day 4 of the pupal stage and was carried by the moth in the adult stage. In addition to the microsystem, an anchor for use in manipulating the adults was formed in the moth by placing a glass capillary through the pupa. Pupae with implants emerged and the microsystem was used to characterize the potential for flight control. To determine the microplatform design, the strength-interval profiles of the pulses needed for direct muscle actuation were determined. Two sets of flight muscles, which are symmetrically present on either side of the thorax, were differentially electrically actuated, which influenced the individual wing beat frequency and amplitude, resulting in controlled turning behavior during flight.

6.3.2. Introduction

There have been several technical approaches explored to develop insect-like small (cm) scale autonomous flying machines. These attempts have been unsuccessful in reaching long-mission duration and insect-like flight because neither the flight actuators are efficient enough, nor the power and energy density of power sources high enough, for sustained reliable flight (Ellington C P, 1999. The novel aerodynamics of insect flight: applications to micro-air vehicles. The Journal of Experimental Biology. 202:3439-348). Nature provides us with insects, which are very good flyers and which have much better aerodynamic performance due to their high efficiency (10-15%) flight actuators. Insects also carry correspondingly dense and efficient energy sources in their chemical fat stores (J. L. Eaton, 1971. Morphology of the head and thorax of the adult tobacco hornworm, *Manduca sexta* (Lepidoptera: Sphingidae). I. Skeleton and muscles. Ann. ent. Soc. Am. 64:437-445). Large insects like the *Manduca sexta* moths have powerful flight muscles (Eaton, supra), and have been shown to carry payloads weighing up to 1 gram.

Insects make attractive models for robotics as "biobots," in which an intact biological system is incorporated into a MEMS design. Insects have already been used to carry telemetric payloads, but the success rates of these flights have been low as the method of payload attachment was temporary and unreliable (T. E. Moore, S. B. Crary, D. E. Koditschek, and T. Conklin. 1998. Directed locomotion in cockroaches: Biobots. Acta Entomologica Slovenica 6(2):71-78; B. Crary, T. E. Moore, T. A. Conklin, F. Sukardi, and D. E. Koditschek, 1996. Insect biobotics: Electro-neural control of cockroach walking. Abstr. IEEE Int. Conf. Robotics and Automation, Workshop WT3, Bio-Mechatronics, 1996: 42-54; P. Mohseni, K. Nagarajan, B. Ziaie, K. Najafi, and S. B. Crary. 2001. An ultralight biotelemetry backpack for recording EMG signals in moths. IEEE Trans. Biomed. Eng. 48(6): 734-737; R. Holzer and I. Shimoyama. 1997. Locomotion control of a bio-robotic system via electric stimulation. Proc. IEEE/RSJ Internat. Conf. on Intelligent Robots and Systems, Grenoble, France, September 1997, 1514-1519.Y. Kuwana, N. Ando, R. Kanzaki, and I. Shimoyama. 1999. A radiotelemetry system for muscle potential recordings from freely flying insects. Proc. IEEE BMES/EMBS Conf., Atlanta, Ga., October 1999, p. 846). These payloads were either strapped on the adult insect as backpacks or were adhesively bonded onto the body surface. These attachments were perceived as foreign weights, since they were superficially attached and the insect would try to rid itself of the payload. Also, handling a live adult is challenging due to constant motion and is also stressful for the adult insect.

In this example, we developed a protocol using the tobacco hawkmoth, *Manduca sexta*, as our working model, in which we surgically inserted Microsystems in the pupal stage (an early stage of metamorphosis) when the insect was immobile (FIG. 16). This procedure led to emergence of an adult moth with the platform or silicon insert permanently attached onto the insect, since the adult exoskeleton had healed over the inserts. Since the insert had been introduced into the insect body prior to its emergence as an adult, it was perceived as the insect's own weight rather than extra (foreign) weight that it had to carry during flight. Also survival rates of the moths with the insert inserted during its metamorphic stage were comparable to normal unaltered moths.

Using surgical implantation and wound repair techniques (Early Metamorphosis Insertion Technology, "EMIT") (see materials and methods described herein, e.g., in Sections 6.1 and 6.2), we developed Microsystems for implantation in early metamorphosis stages of insects, to create an insect "cyborg", "biobot" or robotic apparatus. The microsystems were used to intrinsically stimulate the insect's physiological response, such as flight. The microsystem provided sensor, stimulation and navigation capabilities, while the insect provided a naturally occurring flight actuator and energy source.

Different actuation mechanisms can be used to control the flight. The insect can be influenced by indirect external stimulation or direct internal excitation. External stimulation methods can be targeted, inter alia, towards sensory organs, for example, visual stimulation using light patterns, or pheromonal stimulation as olfactory cues. For internal excitation, selected regions of interest in the neuromuscular system can be actuated using either electrical or chemical stimulation. In this example, we aimed to stimulate dorsoventral flight muscles, which are believed to express directional response (Eaton 1971, supra). Using properly timed electrical stimuli from MEMS devices implanted in the insect's flight muscles, insect flight and other forms of locomotion can be monitored and controlled.

In this example we demonstrate (a) flight control of the insect "cyborg", biobot or robotic apparatus, using wires inserted in early-metamorphosis stages of the moth, *Manduca sexta*, and (b) the development of a battery-powered microsystem that was also implanted using EMIT.

6.3.3 Experimental Procedure and Results 6.3.3.1 Tethered Wing Actuation

To determine the location of appropriate muscles and the electrical waveforms needed to actuate muscles, we first inserted titanium wire electrodes in the muscle groups of tethered moths. (FIGS. 17*a-b*).

Square current pulses applied to the muscle fibers set up an action potential wave, which initiated the twitch contraction. Current pulses with different pulse-widths were applied and current amplitude threshold to initiate the flapping of the wings was measured (FIG. 18).

During these experiments, left and right muscle groups were differentially or selectively excited (data not shown). The charge transfer from the electrodes to the muscles was controlled by conduction through the muscle tissue and diffusion of charged ions in the Helmholtz plane. As the pulse width was reduced, the effective amount of current required for actuation increased exponentially, indicating diffusion was controlling the actuation. As the duration of pulses increased, the actuation was limited by tissue conductivity (see, e.g., Borkholder, D. A. 1998. Cell Based Biosensors Using Microelectrodes. Ph.D. Thesis, Stanford University, Stanford Calif.).

6.3.3.2 Untethered Wing Actuation

After determining the required pulse width and amplitude, a microsystem platform was designed, assembled and inserted in moths using EMIT.

6.3.3.2.1 Microprobe Microsystem Platform

The required actuation waveforms were generated by a microsystem as shown in FIGS. 19*a-c*. The microsystem consisted of three layers, a power layer, a probe layer and a control layer.

The power layer comprised two coin batteries and a slide-switch positioned on a printed circuit board (PCB). Each battery had an energy capacity of 8 mAh and weighed 120 mg. Conductive adhesive was used to attach the batteries to the platform.

The control layer was an 8×8 mm PCB holding a microcontroller (Atmel Tiny13V) and an LED. The microcontroller was electrically connected to the PCB via flip-chip bonding. Wire-bonding was used to connect the PCB to the probe layer. The microfabricated silicon probe was sandwiched between these two layers.

The overall system had dimensions of 8×7 mm$^2$ and total mass of 500 milligrams. The silicon microprobe platform (500 μm thick) comprised two tips (each 200 μm wide, 200 μm thick and 5 mm long) separated by a distance of 5 mm, which was the approximate distance between the right and left flight muscles of the moth (FIG. 13).

Platinum (electrode metal) was evaporated and patterned on a 4-inch silicon wafer with a layer of 900 nm LPCVD nitride. PECVD nitride was deposited on the metal and patterned to provide passivation. For muscle-specific excitation, the metal lines running along the length of the probe tip that actuate the muscle cells were only exposed close to the end of the tip (100×100 μm$^2$) (FIG. 20). The desired probe tip thickness was achieved by deep reactive ion etching (DRIE). Backside-only KOH etching (with LPCVD nitride mask) was done to release the device.

6.3.3.2.2 Microcontroller Algorithms

As discussed above, the concept of differential wing actuation was demonstrated with titanium wire-based electrical excitation on tethered moths (see also Section 6.2, Example 2). In the present example, an algorithm was implemented on the microcontroller of the microsystem platform to send sequential electrical pulses to the right and left tips of the probe to observe the effect of the differential actuation during untethered flight.

The algorithm comprised outputting time-scheduled 3V square pulses with a duty cycle of 6% and frequency of 30 Hz, which corresponds to the natural wing-beat frequency (B. Heinrich, G. A. Bartholomew. 1971. An Analysis Of Pre-Flight Warm-Up In The Sphinx Moth, Manduca Sexta, J. Exp. Biol. 55: 233-239). The timing-scheme of each excitation cycle is described in FIG. 21. The second idle period was kept longer (40 sec) to avoid habituation. This scheme repeated itself until it was stopped by the switch on the power layer. The LED on the control layer was used to externally monitor the electrical excitations.

The power breakdown of the different components is shown in FIG. 22.

6.3.3.2.3 EMIT-Based Insertions

The manufactured platforms were inserted in the thorax using the surgical methods described hereinabove, at an angle to avoid interference with wing motion. Insertions were performed after the first quarter of the pupal stage (on the third day of a 15-day pupal stage), when the cuticle hardens. Additionally, a glass capillary with a diameter of 250 μm was inserted from the posterior end of the abdomen of the pupa and extended to the thorax, to serve as an easy tether by which the insect could be mechanically anchored and manipulated. The cuticle was punctured with a hypodermic needle at the appropriate insertion location and the probe or capillary was inserted. The puncture was then immediately sealed with a drop of wax to prevent any oozing around the inserts, due to still relatively high inner pressure in the body cavity. Pupae survived both insertions and emerged as full grown adults (FIGS. 14a-d).

Dissections of the thorax were performed to observe the insertion of the probes near the target muscle groups (FIG. 15). Muscle growth around the probe tips indicated adaptation by the moth body.

Micro-Computer Tomography (Micro-CT) imaging of the moth thorax was also performed, in parallel with the anatomical dissections, to evaluate the insertion efficacy (FIGS. 23A-C). Micro-CT images were obtained with a Skyscan 1172 Micro CT scanner (resolution of 17.4 microns). As seen on the obtained CT image in FIG. 23A, the probes were inserted directly to the dorsoventral wing elevator muscle for initiation of the wing strokes. FIG. 23C shows the orientation of the moth in FIGS. 23A-B. Prior to imaging, the body of the microsystem platform was broken, keeping the inserted probes in their original locations, so that the subject insect would fit into the scanner. The tissue growth around the probes (shown by arrows) indicated the acceptance of the probes by the moth body (FIG. 23B).

The rate of emergence of moths from implanted pupae was found to be 90%. However, 6 out of 7 adults were not able to spread their wings properly. During eclosion, the newly emerged adult normally aligns itself vertically on a surface, so that the wings can inflate via gravity-based flow of hemolymph. Since the fully functional probes were heavy, they interfered with the ability of the adult to align itself vertically upon emergence and form functional wings. However, wing inflation can be optimized by tethering the insects in a vertical orientation during eclosion for better hemolymph flow.

6.3.4 Conclusions and Discussion

Insects are autonomous flying machines that surpass any existing mechanical flying machine of comparable size, both in aerodynamic performance and flight actuation machinery. The aim of this study was to employ insects, particularly moths, as a biological system in which to create a hybrid system with intimate electromechanical interfaces with the body for control of muscles. The present example demonstrated the use of EMIT to insert microsystems in the early pupal stages to obtain reliable interfaces.

We have also demonstrated that flight can be controlled in the moth, *Manduca sexta*, using in-built electrical stimulation of muscle. Using this information, we designed a silicon-microprobe based platform that was inserted in pupae using EMIT. We demonstrated emergence of the moth with a platform that weighed 500 mg.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for producing an arthropod, comprising:
  introducing a microsystem into an immature arthropod under conditions that allow growth of the immature arthropod into an adult arthropod thus producing the adult arthropod that is implanted with the microsystem substantially free of injury and without hindering physical functions of the adult arthropod, wherein the microsystem is functional and attached to the body of the adult arthropod, and wherein the microsystem is introduced when the immature arthropod is at a development stage that includes a molting period prior to that of the adult arthropod such that development into the adult arthropod heals an initial injury to the immature arthropod caused by the introducing the microsystem.

2. The method of claim 1 wherein the microsystem is permanently attached.

3. The method of claim 1 wherein the immature arthropod is an insect.

4. The method of claim 3 wherein the insect is a holometabolous insect.

5. The method of claim 1 wherein the introducing step is surgical implantation.

6. The method of claim 1 wherein the microsystem is an attachment apparatus.

7. The method of claim 1 wherein the immature arthropod undergoes a metamorphosis to the adult arthropod such that the microsystem is incorporated and biocompatibly coupled into the body of the arthropod.

8. A method for producing a robotic apparatus, the method comprising:

introducing a microsystem into an immature arthropod or portion thereof under conditions that allow growth of the immature arthropod into an adult arthropod to produce a robotic apparatus, wherein the robotic apparatus comprises:

the microsystem, and a biological system, the biological system comprising the adult arthropod or portion thereof, and wherein the microsystem is biocompatibly attached to the body of the adult arthropod or portion thereof without injury and without hindering physical functions of the robotic apparatus, wherein the introducing includes attachment of the microsystem to the immature arthropod at a development stage that includes a molting period prior to that of the adult arthropod such that development into the adult arthropod heals an initial injury to the immature arthropod caused by the introducing the microsystem.

9. The method of claim 8 wherein the microsystem is attached permanently.

10. The method of claim 8 wherein the biological system comprises a portion of the adult arthropod capable of generating or controlling a physiological function of the adult arthropod, and wherein the robotic apparatus is capable of carrying out the physiological function or a portion or sub-function thereof.

11. The method of claim 10 wherein the physiological function is locomotion.

12. The method of claim 11 wherein the microsystem activates a muscle that regulates the locomotion.

13. The method of claim 12 wherein the muscle is a flight muscle and the locomotion is flying.

14. The method of claim 12 wherein the muscle is a leg muscle and the locomotion is walking.

15. The method of claim 8 wherein the immature arthropod is an insect.

16. The method of claim 15 wherein the insect is a holometabolous insect.

17. The method of claim 8 wherein the introducing step is surgical implantation.

18. The method of claim 8 wherein the microsystem is an attachment apparatus.

19. The method of claim 8 wherein the immature arthropod undergoes a metamorphosis to the adult arthropod such that the microsystem is incorporated and biocompatibly coupled into the body of the adult arthropod.

\* \* \* \* \*